(12) United States Patent
Horsager et al.

(10) Patent No.: US 11,771,763 B2
(45) Date of Patent: Oct. 3, 2023

(54) METHODS AND COMPOSITIONS FOR DECREASING CHRONIC PAIN

(71) Applicants: EOS Neuroscience, Inc., San Francisco, CA (US); Wake Forest University Health Sciences, Winston-Salem, NC (US)

(72) Inventors: Alan Horsager, Los Angeles, CA (US); Kenneth Greenberg, Oakland, CA (US); Benjamin C. Matteo, San Francisco, CA (US); Edward S. Boyden, Chestnut Hill, MA (US); Douglas G. Ririe, Winston-Salem, NC (US); James C. Eisenach, Winston-Salem, NC (US); Christian Wentz, Cambridge, MA (US)

(73) Assignees: EOS NEUROSCIENCE, INC., San Francisco, CA (US); WAKE FOREST UNIVERSITY HEALTH SCIENCES, Winston-Salem, NC (US)

( * ) Notice: Subject to any disclaimer, the term of this patent is extended or adjusted under 35 U.S.C. 154(b) by 0 days.

(21) Appl. No.: 16/455,077

(22) Filed: Jun. 27, 2019

(65) Prior Publication Data
US 2021/0069329 A1 Mar. 11, 2021

Related U.S. Application Data

(63) Continuation of application No. 13/637,977, filed as application No. PCT/US2011/031297 on Apr. 5, 2011, now abandoned.

(60) Provisional application No. 61/321,117, filed on Apr. 5, 2010.

(51) Int. Cl.
| | |
|---|---|
| *A61N 5/06* | (2006.01) |
| *A61K 48/00* | (2006.01) |
| *A61K 49/00* | (2006.01) |
| *A61K 41/00* | (2020.01) |
| *C07K 14/195* | (2006.01) |
| *C07K 14/37* | (2006.01) |
| *A61K 31/7088* | (2006.01) |
| *C07K 14/215* | (2006.01) |

(52) U.S. Cl.
CPC .......... *A61K 41/00* (2013.01); *A61K 31/7088* (2013.01); *A61N 5/062* (2013.01); *C07K 14/195* (2013.01); *C07K 14/215* (2013.01); *C07K 14/37* (2013.01); *C07K 2319/60* (2013.01); *C12N 2750/14143* (2013.01); *C12N 2810/6027* (2013.01)

(58) Field of Classification Search
None
See application file for complete search history.

(56) References Cited

U.S. PATENT DOCUMENTS

| | | |
|---|---|---|
| 4,522,811 A | 6/1985 | Eppstein et al. |
| 5,912,122 A | 6/1999 | Daggett et al. |
| 6,204,251 B1 | 3/2001 | Cuthbertson |
| 6,362,316 B1 | 3/2002 | Daggett et al. |
| 7,094,604 B2 | 8/2006 | Snyder et al. |
| 7,144,733 B2 | 12/2006 | Miesenböck et al. |
| 7,342,111 B2 | 3/2008 | Lewin et al. |
| 7,824,869 B2 | 11/2010 | Hegemann et al. |
| 8,910,638 B2 | 12/2014 | Boyden |
| 2004/0022766 A1 | 2/2004 | Acland et al. |
| 2005/0202398 A1 | 9/2005 | Hegemann et al. |
| 2005/0208022 A1 | 9/2005 | Masland |
| 2007/0053996 A1 | 3/2007 | Boyden et al. |
| 2007/0054319 A1 | 3/2007 | Boyden et al. |
| 2007/0259420 A1 | 11/2007 | Greenbaum |
| 2007/0261127 A1 | 11/2007 | Boyden et al. |
| 2007/0276024 A1 | 11/2007 | Bond |
| 2008/0085265 A1 | 4/2008 | Schneider et al. |
| 2008/0125832 A1 | 5/2008 | Horsager et al. |
| 2009/0074723 A1 | 3/2009 | Acland et al. |
| 2009/0088399 A1 | 4/2009 | Balya et al. |
| 2009/0088680 A1 | 4/2009 | Aravanis et al. |
| 2009/0099038 A1 | 4/2009 | Deisseroth et al. |
| 2009/0281163 A1 | 11/2009 | Cepko et al. |
| 2009/0312818 A1 | 12/2009 | Horsager et al. |
| 2010/0006049 A1 | 1/2010 | Jung et al. |
| 2010/0015095 A1 | 1/2010 | Pan et al. |
| 2010/0016783 A1 | 1/2010 | Bourke et al. |
| 2010/0145418 A1 | 6/2010 | Zhang |
| 2010/0190229 A1 | 7/2010 | Zhang et al. |
| 2010/0234273 A1 | 9/2010 | Boyden et al. |
| 2011/0021970 A1 | 1/2011 | Vo-Dinh et al. |
| 2011/0086421 A1 | 4/2011 | Hegemann et al. |

(Continued)

FOREIGN PATENT DOCUMENTS

| | | |
|---|---|---|
| EP | 1492881 B1 | 10/2008 |
| WO | WO 92/08796 A1 | 5/1992 |
| WO | WO 94/28143 A1 | 12/1994 |

(Continued)

OTHER PUBLICATIONS

Zhao et al Sodium channel expression in the ventral posterolateral nucleus of the thalamus after peripheral nerve injury Molecular Pain 2006, 2:27 pp. 1-10.

(Continued)

*Primary Examiner* — Maria G Leavitt
(74) *Attorney, Agent, or Firm* — HESLIN ROTHENBERG FARLEY & MESITI P.C.

(57) ABSTRACT

The present invention provides compositions and methods for the selective silencing of neurons in pain pathway by using a combination of inhibitory light-sensitive protein gene transfer and wavelength specific illumination.

19 Claims, 10 Drawing Sheets

Specification includes a Sequence Listing.

(56) References Cited

U.S. PATENT DOCUMENTS

| | | |
|---|---|---|
| 2012/0093772 A1 | 4/2012 | Horsager et al. |
| 2013/0225664 A1 | 8/2013 | Horsager |

FOREIGN PATENT DOCUMENTS

| | | |
|---|---|---|
| WO | WO 96/29404 A1 | 9/1996 |
| WO | WO 1998/48027 A2 | 10/1998 |
| WO | WO 1998/48027 A3 | 3/1999 |
| WO | WO 2003/047525 A2 | 6/2003 |
| WO | WO 2003/047525 A3 | 9/2003 |
| WO | WO 2004/009022 A2 | 1/2004 |
| WO | WO 2004/009022 A3 | 7/2004 |
| WO | WO 2004/084951 A2 | 10/2004 |
| WO | WO 2004/084951 A3 | 11/2004 |
| WO | WO 2005/080573 A1 | 9/2005 |
| WO | WO 2007/131180 A2 | 11/2007 |
| WO | WO 2008/022772 A1 | 2/2008 |
| WO | WO 2007/131180 A3 | 7/2008 |
| WO | WO 2008/086470 A1 | 7/2008 |
| WO | WO 2008/089003 A2 | 7/2008 |
| WO | WO 2008/089003 A3 | 9/2008 |
| WO | WO 2008/124724 A1 | 10/2008 |
| WO | WO 2009/124189 A1 | 10/2009 |
| WO | WO 2009/127705 A1 | 10/2009 |
| WO | WO 2010/006049 A1 | 1/2010 |
| WO | WO 2010/009141 A1 | 1/2010 |
| WO | WO 2010/011404 A2 | 1/2010 |
| WO | WO 2010/123993 A1 | 10/2010 |
| WO | WO 2010/011404 A3 | 2/2011 |

OTHER PUBLICATIONS

Aurilia et al Ionic Channels and Neuropathic Pain: Phisiopatology and Applications 2008; Journal of Cell Physiology 215, 8-14.
Cummins et al., Comprehensive review The roles of sodium channels in nociception: Implications for mechanisms of pain Pain 131 (2007) 243-257.
Tan et al Selective and Quickly NeurotechniqueReversible Inactivation of Mammalian Neurons In Vivo Using the *Drosophila* Allatostatin Receptor Neuron 51, 157-170, Jul. 20, 2006.
Noguchi et al A noxious stimulus induces the preprotachykinin-A gene expression in the rat dorsal root ganglion: a quantitative study using in situ hybridization histochemistryMolecular Brain Research vol. 4, Issue 1, Aug. 1988, pp. 31-35; Abstract.
Alloca et al Novel Adeno-Associated Virus Serotypes Efficiently Transduce Murine Photoreceptors Journal of Virology, Oct. 2007, p. 11372-11380.
U.S. Appl. No. 60/701,799, filed Jul. 22, 2005, Deisseroth et al.
3rd party observation dated Oct. 2, 2012 against EP Application No. 9800733.9.
Acland et al. Gene therapy restores vision in a canine model of childhood blindness. Nat Genet. 2001;28:92-95.
Acland et al. Long-term restoration of rod and cone vision by single dose rAAV-mediated gene transfer to the retina in a canine model of childhood blindness. Molecular Therapy: the Journal of the American Society of Gene Therapy. 2005;12:1072-1082.
Aguirre et al. Canine and human visual cortex intact and responsive despite early retinal blindness from RPE65 mutation. PLoS Medicine. 2007;4:e230.
Aronoff et al. Controlled and localized genetic manipulation in the brain. Journal of Cellular and Molecular Medicine. 2006;10:333-352.
Arrenberg, et al. Optical control of zebrafish behavior with halorhodopsin. PNAS. 2009; 106(42):17968-17973.
Baccus et al. Timing and computation in inner retinal circuitry. Annu Rev Physiol. 2007;69:271-290.
Baron. Mechanisms of disease: neuropathic pain—a clinical perspective. Nat Clin Pract Neurol. Feb. 2006;2(2):95-106.
Batten et al. Pharmacological and rAAV gene therapy rescue of visual functions in a blind mouse model of Leber congenital amaurosis.[see comment]. PLoS Medicine. 2005;2:e333.

Berndt et al. Bi-stable neural state switches. Nat Neurosci. Feb. 2009;12(2):229-34.
Beutler, et al. Intrathecal gene transfer by adeno-associated virus for pain. Curr Opin Mol Ther. Oct. 2005;7(5):431-9.
Beutler, et al. Retrovirus-mediated expression of an artificial beta-endorphin precursor in primary fibroblasts. J Neurochem. Feb. 1995;64(2):475-81.
Bi, et al. Ectopic Expression of a Microbial-Type Rhodopsin Restores Visual Responses in Mice with Photoreceptor Degeneration. Nueron. 2006;50(1):23-33.
Borrás. Recent developments in ocular gene therapy. Experimental Eye Research. 2003;76(6):643-652.
Bowie, et al. Deciphering the message in protein sequences: tolerance to amino acid substitutions. Science. Mar. 16, 1990;247(4948):1306-10.
Boyden, et al. Millisecond-timescale, genetically targeted optical control of neural activity. Nat Neurosci. Sep. 2005;8(9):1263-8. Epub Aug. 14, 2005.
Carlton, et al. Behavioral manifestations of an experimental model for peripheral neuropathy produced by spinal nerve ligation in the primate. Pain. Feb. 1994;56(2):155-66.
Casini et al. Developmental expression of neurokinin-1 and neurokinin-3 receptors in the rat retina. The Journal of Comparative Neurology. 2000;421(2):275-287.
Cemazar et al. Electrically-assisted nucleic acids delivery to tissues in vivo: where do we stand? Current Pharmaceutical Design. 2006;12:3817-3825.
Chader. Animal models in research on retinal degenerations: past progress and future hope. Vision Research. 2002;42:393-399.
Chow, et al. High-performance genetically targetable optical neural silencing by light-driven proton pumps. Nature. Jan. 7, 2010;463(7277):98-102.
Christensen, et al. Spinal neurons specifically excited by noxious or thermal stimuli: marginal zone of the dorsal horn. J Neurophysiol. Mar. 1970;33(2):293-307.
Chung, et al. Segmental spinal nerve ligation model of neuropathic pain. Methods Mol Med. 2004;99:35-45.
Congdon et al. Causes and prevalence of visual impairment among adults in the United States. Archives of Ophthalmology. 2004;122:477-485.
De Koning, et al. Methods for producing a reproducible crush in the sciatic and tibial nerve of the rat and rapid and precise testing of return of sensory function. Beneficial effects of melanocortins. J Neurol Sci. Jul. 1986;74(2-3):237-46.
Dhingra et al. Light response of retinal ON bipolar cells requires a specific splice variant of Galpha(o). Journal of Neuroscience. 2002;22:4878-4884.
Dhingra et al. The light response of ON bipolar neurons requires G[alpha]o. Journal of Neuroscience. 2000;20:9053-9058.
Dhingra, et al. Probing neurochemical structure and function of retinal ON bipolar cells with a transgenic mouse. J Comp Neurol. Oct. 10, 2008;510(5):484-96.
Dinculescu, et al. Adeno-associated virus-vectored gene therapy for retinal disease. Hum Gene Ther. Jun. 2005;16(6):649-63.
Doroudchi, et al. Virally delivered channelrhodopsin-2 safely and effectively restores visual function in multiple mouse models of blindness. Mol Ther. Jul. 2011;19(7):1220-9. doi: 10.1038/mt.2011.69. Epub Apr. 19, 2011.
Duvoisin, et al. A novel metabotropic glutamate receptor expressed in the retina and olfactory bulb. J Neurosci. Apr. 1995;15(4):3075-83.
European search report and search opinion dated Dec. 6, 2011 for Application No. 9800733.9.
Finegold, et al. A paracrine paradigm for in vivo gene therapy in the central nervous system: treatment of chronic pain. Hum Gene Ther. May 1, 1999;10(7):1251-7.
Flannery. Looking within for Vision. Neuron. 2006;50(1):1-3.
Fong, et al. The use and development of retroviral vectors to deliver cytokine genes for cancer therapy. Crit Rev Ther Drug Carrier Syst. 2000;17(1):1-60.
Gao et al. New recombinant serotypes of AAV vectors. Current Gene Therapy. 2005;5:285-297.

(56) References Cited

OTHER PUBLICATIONS

Gargini et al. Retinal organization in the retinal degeneration 10 (rd10) mutant mouse: a morphological and ERG study. Journal of Comparative Neurology. 2007;500:222-238.
Gracely, et al. New methods of pain measurement and their application to pain control. Int Dent J. Mar. 1978;28(1):52-65.
Greenberg et al. In vivo Transgene Expression in ON-Type Retinal Ganglion Cells: Applications to Retinal Disease. Association of Research in Vision and Ophthalmology; 2007.
Greener, et al. An efficient random mutagenesis technique using an E. coli mutator strain. Methods Mol Biol. 1996;57:375-85.
Hakki Onen, et al. Effects of rapid eye movement (REM) sleep deprivation on pain sensitivity in the rat. Brain Res. May 11, 2001;900(2):261-7.
Han, et al. Millisecond-timescale optical control of neural dynamics in the nonhuman primate brain. Neuron. Apr. 30, 2009;62(2):191-8.
Han, et al. Multiple-color optical activation, silencing, and desynchronization of neural activity, with single-spike temporal resolution. PLoS One. Mar. 21, 2007;2(3):e299.
Harrison, et al. Neuronal-specific and nerve growth factor-inducible expression directed by the preprotachykinin—A promoter delivered by an adeno-associated virus vector. Neuroscience. 1999;94(3):997-1003.
Hashimoto, et al. The whole nucleotide sequence and chromosomal localization of the gene for human metabotropic glutamate receptor subtype 6. Eur J Neurosci. Jun. 1997;9(6):1226-35.
Hu, et al. Design of retroviral vectors and helper cells for gene therapy. Pharmacol Rev. Dec. 2000;52(4):493-511.
Humayun et al. Pattern electrical stimulation of the human retina. Vision Research. 1999;39:2569-2576.
Hungund, et al. Are anandamide and cannabinoid receptors involved in ethanol tolerance? A review of the evidence. Alcohol Alcohol. Mar.-Apr. 2000;35(2):126-33.
International search report and written opinion dated Jun. 26, 2012 for PCT Application No. US2011/056475.
International search report and written opinion dated Jan. 3, 2010 for PCT Application No. US2009/04453.
International search report and written opinion dated Nov. 25, 2011 for PCT Application No. 2011/031297.
Kayser, et al. Differential anti-neuropathic pain effects of tetrodotoxin in sciatic nerve- versus infraorbital nerve-ligated rats—behavioral, pharmacological and immunohistochemical investigations. Neuropharmacology. Feb. 2010;58(2):474-87. Epub Sep. 9, 2009.
Kiasalari, et al. Identification of perineal sensory neurons activated by innocuous heat. J Comp Neurol. Jan. 10, 2010;518(2):137-62.
Kim, et al. A Core Paired-Type and POU Homeodomain-Containing Transcription Factor Program Drives Retinal Bipolar Cell Gene Expression. The Journal of Neuroscience. 2008;28(31):7748-64.
Krebs, et al. Gene replacement in Halobacterium halobium and expression of bacteriorhodopsin mutants. Proc Natl Acad Sci U S A. Mar. 1, 1993;90(5):1987-91.
Krebs, et al. Itramembrane substitutions in helix D of bacteriorhodopsin disrupt the purple membrane. J Mol Biol. Mar. 21, 1997;267(1):172-83.
Lagali et al. Targeted Reporter Gene Expression for Morphological and Functional Assessment of Inner Retinal Neurons in Wild-Type and Retinal Degeneration Mice. Fort Lauderdale, Florida: Association for Research in Vision and Ophthalmology; 2007.
Lagali, et al. Light-activated channels targeted to On bipolar cells restore visual function in retinal degeneration. Nat Neurosci. Jun. 2008;11(6):667-75.
Le Bars, et al. Animal models of nociception. Pharmacol Rev. Dec. 2001;53(4):597-652.
Li et al. Electroporation gene therapy: new developments in vivo and in vitro. Current Gene Therapy. 2004;4:309-316.
Lieber, et al. Integrating adenovirus-adeno-associated virus hybrid vectors devoid of all viral genes. J Virol. Nov. 1999;73(11):9314-24.
Lin, et al. Characterization of engineered channelrhodopsin variants with improved properties and kinetics. Biophys J. Mar. 4, 2009;96(5):1803-14.

Linden, et al. TASK-3 knockout mice exhibit exaggerated nocturnal activity, impairments in cognitive functions, and reduced sensitivity to inhalation anesthetics. J Pharmacol Exp Ther. Dec. 2007;323(3):924-34. Epub Sep. 17, 2007.
Lundstrom. Alphavirus vectors: applications for DNA vaccine production and gene expression. Intervirology. 2000;43(4-6):247-57.
Maclaren et al. Retinal repair by transplantation of photoreceptor precursors. Nature. 2006;444:203-207.
Marc, et al. Neural reprogramming in retinal degeneration. J Neurosci. Apr. 1995;15(4):3075-83.
Masland. The many roles of starburst amacrine cells. Trends in Neurosciences. 2005;28(8)395-396.
Medeiros et al. Preservation of ganglion cell layer neurons in age-related macular degeneration. Investigative Ophthalmology & Vision Science. 2001;42(3):795-803.
Melzack, et al. Skin sensory afterglows. Science. Jan. 26, 1968;159(3813):445-7.
Mendell. Physiological properties of unmyelinated fiber projection to the spinal cord. Exp Neurol. Nov. 1966;16(3):316-32.
Mills et al. AII amacrine cells limit scotopic acuity in central macaque retina: A confocal analysis of calretinin labeling. J Comp Neurol. 1999;411:19-34.
Miyoshi, et al. of a self-inactivating lentivirus vector. J Virol. Oct. 1998;72(10):8150-7.
Moore, et al. peripheral nerve injury promotes a selective loss of GABAergic inhibition in the superficial dorsal horn of the spinal cord. J Neurosci. Aug. 1, 2002;22(15):6724-31.
Morrison, et al. An activator element within the preprotachykinin-A promoter. Mol Cell Neurosci. Apr. 1994;5(2):165-75.
Nagel et al. Channelrhodopsin-1: a light-gated proton channel in green algae. Science. 2002;296:2395-2398.
Nagel et al. Channelrhodopsin-2, a directly light-gated cation-selective membrane channel. Proc Natl Acad Sci USA. 2003;100:13940-13945.
Nagel et al. Channelrhodopsins: directly light-gated cation channels. Biochemical Society Transactions. 2005;33:863-866.
Natkunarajah, et al. Assessment of ocular transduction using single-stranded and self-complementary recombinant adeno-associated virus serotype 2/8. Gene Ther. Mar. 2008;15(6):463-7. Epub Nov. 15, 2007.
Nawy, S. The metabotropic receptor mGluR6 may signal through G(o), but not phosphodiesterase, in retinal bipolar cells. J Neurosci. Apr. 15, 1999;19(8):2938-44.
Nichols, et al. Enhancement of the antiallodynic and antinociceptive efficacy of spinal morphine by antisera to dynorphin A (1-13) or MK-801 in a nerve-ligation model of peripheral neuropathy. Pain. Feb. 1997;69(3):317-22.
Palecek, et al. Responses of spinothalamic tract neurons to mechanical and thermal stimuli in an experimental model of peripheral neuropathy in primates. J Neurophysiol. Dec. 1992;68(6):1951-66.
Pawlyk et al. Gene replacement therapy rescues photoreceptor degeneration in a murine model of Leber congenital amaurosis lacking RPGRIP. Investigative Ophthalmology & Visual Science. 2005;46:3039-3045.
Perri, et al. Replicon vectors derived from Sindbis virus and Semliki forest virus that establish persistent replication in host cells. J Virol. Oct. 2000;74(20):9802-7.
Petrs-Silva et al. High-efficiency Transduction of the Mouse Retina by Tyrosine-mutant AAV Serotype Vectors. Molecular Therapy. 2009;17(3):463-71.
Puhl, et al. Identification of the sensory neuron specific regulatory region for the mouse gene encoding the voltage-gated sodium channel NaV1.8. J Neurochem. Aug. 2008;106(3):1209-24. Epub May 7, 2008.
Punzo et al. Cellular responses to photoreceptor death in the rd1 mouse model of retinal degeneration. Investigative Ophthalmology & Visual Science. 2007;48:849-857.
Rizzo et al. Perceptual Efficacy of Electrical Stimulation of Human Retina with a Microelectrode Array during Short-Term Surgical Trials. Invest. Ophthalmol. Vis. Sci. 2003;44:5362-5369.
Roska et al. Vertical interactions across ten parallel, stacked representations in the mammalian retina. Nature. 2001;410:583-587.

(56) References Cited

OTHER PUBLICATIONS

Scholz, et al. Blocking caspase activity prevents transsynaptic neuronal apoptosis and the loss of inhibition in lamina II of the dorsal horn after peripheral nerve injury. J Neurosci. Aug. 10, 2005;25(32):7317-23.

Shoda, et al. Increased phosphorylation of extracellular signal-regulated kinase in trigeminal nociceptive neurons following propofol administration in rats. J Pain. Jun. 2009;10(6):573-85. Epub Apr. 23, 2009.

Sineshchekov et al. Two rhodopsins mediate phototaxis to low- and high-intensity light in Chlamydomonas reinhardtii. Proc Natl Acad Sci USA. 2002;99:8689-8694.

Smith, et al. Tissue-specific regulatory elements in mammalian promoters. Mol Syst Biol. 2007;3:73.

St. Pierre, et al. Differential effects of TRPV channel block on polymodal activation of rat cutaneous nociceptors in vitro. Exp Brain Res. Jun. 2009;196(1):31-44. Epub Apr. 30, 2009.

Stone, et al. Spinal analgesic actions of the new endogenous opioid peptides endomorphin-1 and -2. Neuroreport. Sep. 29, 1997;8(14):3131-5.

Strettoi et al. Modifications of retinal neurons in a mouse model of retinitis pigmentosa. PNAS. 2000;97(20):11020-11025.

Taylor et al. New directions in retinal research. Trends in Neurosciences. 2003;26(7):379-385.

Tian et al. G protein coupling profile of mGluR6 and expression of G alpha proteins in retinal ON bipolar cells. Vis Neurosci. 2006;23:909-916.

Tomita et al. Restoration of visual response in aged dystrophic RCS rats using AAV-mediated channelopsin-2 gene transfer. Investigative Ophthalmology & Visual Science. 2007;48:3821-3826.

Ueda, et al. The mGluR6 5' Upstream Transgene Sequence Directs a Cell-Specific and Developmentally Regulated Expression in Retinal Rod and On-Type Cone Bipolar Cells. The Journal of Neuroscience. 1997;17(9):3014-23.

Veraart et al. Vision rehabilitation in the case of blindness. Expert Review of Medical Devices. 2004;1(1):139-153.

Vigna, et al. Lentiviral vectors: excellent tools for experimental gene transfer and promising candidates for gene therapy. J Gene Med. Sep.-Oct. 2000;2(5):308-16.

Wan, et al. In vitro evolution of horse heart myoglobin to increase peroxidase activity. Proc Natl Acad Sci U S A. Oct. 27, 1998;95(22):12825-31.

Wang, et al. Molecular determinants differentiating photocurrent properties of two channelrhodopsins from chlamydomonas. J Biol Chem. Feb. 27, 2009;284(9):5685-96.

Warrington et al. Treatment of human disease by adeno-associated viral gene transfer. Human genetics. 2006;119:571-603.

Wassle et al. Parallel processing in the mammalian retina. Nature Reviews Neuroscience. 2004;5:747-757.

Weiland et al. Visual task performance in Blind Humans with Retinal Prosthetic Implants. Proceedings of the 26th Annual International Conference of the IEEE EMBS; 2004.

Wen, et al. Exploring the allowed sequence space of a membrane protein. Nat Struct Biol. Feb. 1996;3(2):141-8.

Whaley, et al. Selection of peptides with semiconductor binding specificity for directed nanocrystal assembly. Nature. Jun. 8, 2000;405(6787):665-8.

Winter et al. 3rd. Retinal prostheses: current challenges and future outlook. Journal of Biomaterials Science. 2007;18:1031-1055.

Wu et al. Adeno-associated virus serotypes: vector toolkit for human gene therapy. Molecular Therapy. 2006;14:316-327.

Wu, et al. Self-complementary recombinant adeno-associated viral vectors: packaging capacity and the role of rep proteins in vector purity. Hum Gene Ther. Feb. 2007;18(2):171-82.

Yanai et al. Visual performance using a retinal prosthesis in three subjects with retinitis pigmentosa. American Journal of Ophthalmology. 2007;143:820-827.

Zhang et al. Multimodal fast optical interrogation of neural circuitry. Nature. 2007;446:633-639.

Zhang et al. Red-shifted optogenetic excitation: a tool for fast neural control derived from Volvox carteri. Nature Neuroscience. 2008;11:631-633.

Zhang, et al. Neurokinin-1 receptor enhances TRPV1 activity in primary sensory neurons via PKCepsilon: a novel pathway for heat hyperalgesia. J Neurosci. Oct. 31, 2007;27(44):12067-77.

Zhong et al. A dual role of EGFR protein tyrosine kinase signaling in ubiquitination of AAV2 capsids and viral second-strand DNA synthesis. Molecular Therapy. 2007;15:1323-1330.

Zhong et al. Next generation of adeno-associated virus 2 vectors: point mutations in tyrosines lead to high-efficiency transduction at lower doses. Proc Natl Acad Sci USA. 2008;105:7827-7832.

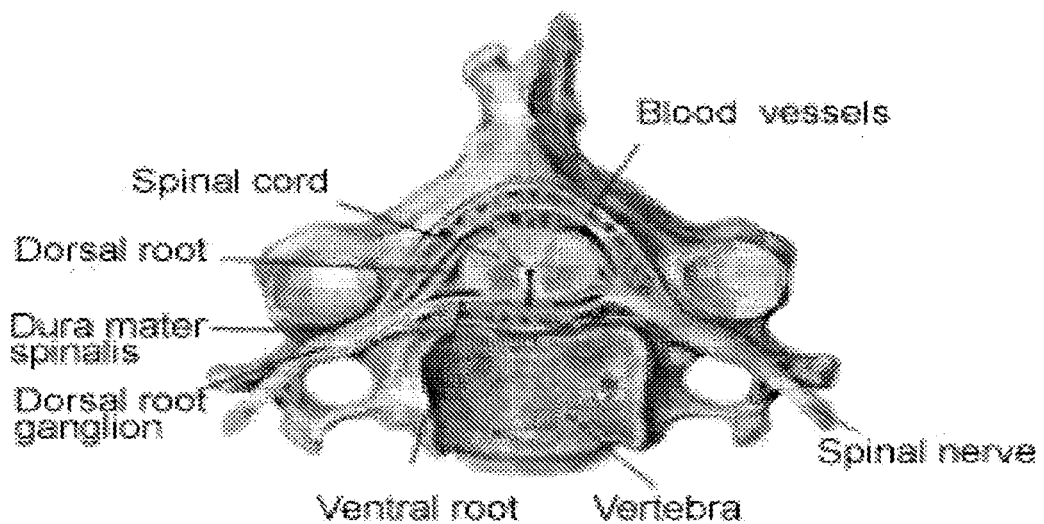
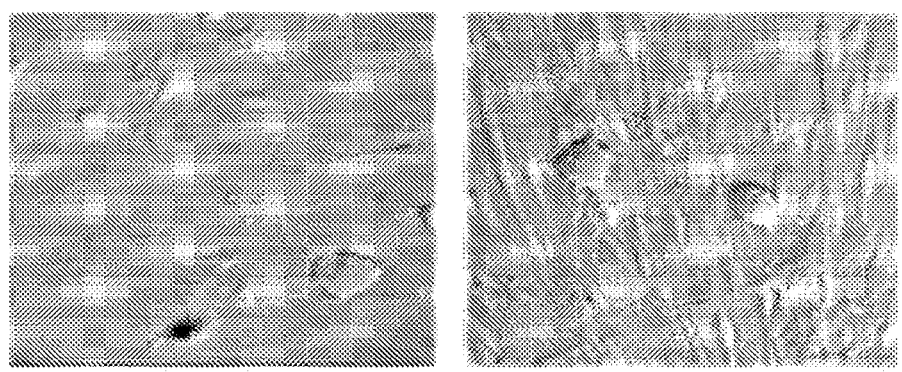
FIG. 9

```
-865                                              CACAGCTCCAAA

-850     GGTAAGCATCCACCCTTTCTAGTCCCCAACAAGGCTAAAGGGAGAGAG

-800     GCACAATTATCCTCTTCCCACCCCTTCTGCCTTCAGGGTGTCCTGGAA
                       COMPLEX BINDING DOMAIN
-750     GAAGCTGTAGGGGAACAAAGATGCCTTAGAATGCCTGATGGGTAAGTTC

-700     TACATGAGAAAGGAGGTTTAAATTCCTCTTTCCCCTAAATGTAAAACAAA
                                           Octamer
-650     CCTGCCTTCATCCTCTGAAGCGCCAGACCCGAAACACTTTTCCAGTCCTA
                                                    SP1/AP2
-600     GACAAATGAGAATATTCTGACTCATTTGGTGGCAGGGGGTTGGGGGG

-550     TGTGTTCCAGCCCTAGATATAACACCTCATAAACCTTAAGACACATAAAG

-500     TAGAATCAAAGGAAACCCGGTTCCTTCATCCCTCTGAAGTGCTTGCT

-450     GGTGTCTTAGTATTATTCACAAGGTTTTGCTGCTCAAGTTATTGGCTGT

-400     CCTCAAAGGGCAATATTCCCTGATGCCTCTTGACAGAAAGTTCCCTAAG

-350     TCCGAAGCATCAGTCACTTCGCTCAGTTTCATCAGTAATCTCAGGTGTC
                      AP1                  AP1       E box
-300     ACTGAACCTTGTTCGGAAGAAGAGGGGCAGGGGGGCCTCAGATTTGCAGAC
                                                 SP1/AP2
-250     GGAAGAAACAGGTCTCTCTGATTGGATGCGAGACCTCGACTTCCCTA -200     AAATTGCGTCATTTCGAACCCAATTTGGTCCACATGTTATGGACTCGGAC
                   CRE/AP1                E box
-150     GGGTTACGGTCTCCGAAACTCTATCAGCAAGCAAAAGCCAGCCGCCGG
                                                    GC BOX
-100     CTAATTAAATATTGAGCAGAAAGTCGCGTGGGAGAGTGTACGTGCCTC
                                                -60 INOX
-50      TCCAGGCTCATCACGCCTCAGATAAATAAGGCGAAGCACGAGCAGGCACT
                                                   HRSE
+1       AGAGGGACTCGGACCAGCTCCACTCCAGCACCGGGCCGAGGACAGCCA +50      GGAGCGCCCAGCAAGTGGCAGCTGCCGAGCATCACCGGGTCC +92
                   E box      E box
```

FIG. 10

```
mouse  CGGAGAACATTTTTGTTTCAGCATTTCAT.CTGAAGCCACGGTTTCACATCATCAAGTC
rat    TTGAGAACATTTTTGTCTCAGCATTTCAT.CTGAAGCTATGCTTTACATCACCAAGTC
human  TTTTTTTTTTTTTGTAATTTCATTTCAAA......CTATTATTTTATAAGACCTGGCC
                                                            -0.6kb                    Primer A
mouse  T............GCAAAAAACCGTTCACAAACCACACCAAAACTTCTC.GGTAAAGAAC
rat    T............GCAAAAAACAGTTCGCAAACGGAACCAAAACTTTTTTCGACAAAGAAC
human  TATTACTGAGTATGCAGGCAGAATATGAAAATTACTCCAAAACTTTTTT..AAATGAAA
                                    TCF1                                    TCF1
mouse  TCCT.AAGGCC..AAAGAGGGACACTGGGTAGATTGTTTTTAATTTGTTTCTTTTTGTC
rat    TTTT.AAGGCG..AAAACGGGAGATAGAGTAGATTGTTTTTAATTGTTTCTTTCTGCC
human  TTTCAAGATGCAAAAA...............GTGAAACTTTAAAAPTTCAGTGGA
            TCF1            TCF1    Primer B
mouse  AAAGGGGACAAAACACCTTTCGTGAGTGTTTATTCTGGGACACAAACCCAG
rat    AAAGGGGACAAAACACCACTTTGCGTGACTGTTTATTCTGGGAC..AAACCCAG
human  AGAACGGGAACAAAAACATTTTAATAAATGAGAGTGTTTATTCCAGAATGGAATATAG
                                        AP2            AP2
mouse  AGT.CTGGAAGGGAGCAT.TCAACGGGTGCTGCTCTGCCACGCAGGGGCAGCGGTGGGA
rat    AGT.ATGAAAGGGAGCAT.TCGGTGGGTGCCGCTCTGCCATGCAGGGGC.GCGGTGGGG
human  AGACAAGGAAGGTACCATGTGAATGGGTGCACCTCG.CTCTCTGGGTCAATGATAGGA
           SP1                AP2              AP2    -0.3kb    Primer C
mouse  CTCAGCCCATCCTGCTAAGGACGGGCAGCCTGAGCC.AGGCTTGGGAGTCTGTCATGG
rat    CTCAGCCCATCCTGCTCAGGAC..CCAGCCTGGCCCCAGGCTTGGGAGTCTGTCATGG
human  AACAGCCTGTCCCA..CAGTCAAGGCAGCCTTGCCC.AGGCTAT.GAGTCTATTGTGGA
                        GATA1                TCF1
mouse  TGCCAGACGAATCATTATCTAATTGCAGCCTTTTCTCTTCCTTAGGTTTCAGCAGGTCC
rat    TGCCAGAGGAATCATTATCTAATTGCAGCCPTTTCTCTTCCTTAGGTTTCAGCGCGTCC
human  TGCTGGGCATT.GTTATCTAAGTGCAGCCTCTTTGCTTCCTCAGGTTTCAGCATTTCC
                Brn2    GFI1                                Primer D
mouse  CGAGAGAGCATTTAAAATCACATTTACTACTTTACCATCTAATCACACATAAGCCTCTC
rat    CAGGAGAGCATTTAAAATCACATTTACTACTTTACCATCTAATCACACATAAGCCTCTC
human  CATGAGATCATTTAAAATCACATTTGCTATTTTACCATCTAATCACACATAAGCCTCTC
                    -0.2kb
mouse  CCTATA..CCCTCCACCCTCCTTCCATTCAG..AGTGTACTTTCTGGAGCACCATCCAG
rat    CCCATA..CCCTCCACCCTCCTTCCATTCAG..AGTGTACTTTCTGGAGCGCATCCAG
human  CCCACACTCCCCCCGCCCTGTTTCCATCCAAGGAGTGCACTTTCTGGAGCACCAGCAAC
            -12    -0.1kb CREB/AP1/ATF/TCF1  Primer E                -75
mouse  CAAGCAGGGTGGAACTCGTGACGGGAAATGGGAACGGCACCCACGAAGGCGTGATTCCT
rat    CAAGCTGGGTGGAATTCGTCACCCGAAATCGAAACTGTACCCACGAACGCGTGATTCCT
human  CAGGGTGGA....ACTCGTGACGGGAAATGGGAATGGCACCCAAGAAAGCATGATTTCT
           -0.06kb    CREB/AP1/ATF    -0.2/0.04kb  TCF1/CREB/AP1/ATF        ARE/GR
mouse  TCTAGATCCTTGAGTGACGGACCGGTGAGGTTTCCGTCAGGCAAGCCCAGCCACCTTCG
rat    CGTAGCTCCCTGAGTGA.Cypel I....GGTTCCCATCAGGCAAGCCCGGCCACCTTCG
human  .GTAGTTTCGTGAATGA.....TAGCAAGGCTCCATCAGACAAGCTGAGCCACTGTCA
                NFKB
                           -1                    AR splice donor                +42
mouse  TGGAGGAGCCCCGGACaagtgtaagt.ttcgcagagctgggg.tctccagcttacttct
rat    TGGACAAGCGC.GGACaagtgtaagt.TTTGCACAGCTGGGG.TCTCTAGCTTGCTTCT
human  CTGAGGAGGAC.AAACGACTGCAAGTCTTTGCAAAGCTTGGCATCTCAGACTTGCCTCT
                           Primer G
mouse  ......gctaatgctaccccaggcctttagacggagaacagatggcagatggag
rat    ......GCTAATGCTACCCCAGGCCTTTAGACAGAGAACAGATGGCAGATGGAGTTTCT
human  CATTTCTTGCTTCACACACTAGCCTCTTGGCTAGAGAACAGACATCAGATGGAGTTTCT rat    TATTGCCATGCGCAAACCCTGAGCCCACCTCATGATCCCGGACCCCATGGTTTTCAGTA
human  TCTGGCTATGCCTGAATGTTAAGCTGAACGTATGTTCCAGGAGCTCGTGGTCTCCAGTA rat    GA..CAACCTGGGCTAAGAAGAGATCTCCGACCTTATAGAGC
human  GAGGCAATCTGGGAT.AGAAGAGAAGATATTTCTTACGTAGAAGACAAGCAA
```

FIG. 11

SEQUENCE LISTING

<160> NUMBER OF SEQ ID NOS: 4

<210> SEQ ID NO 1
<211> LENGTH: 955
<212> TYPE: DNA
<213> ORGANISM: Rattus norvegicus

<400> SEQUENCE: 1

```
cagagctcca aaggtaagca tccagccttt ctagtccccc aacaaggcta aaggggagag      60
aggcacaatt atcctcttcc cacccttct gccttcaggg tgtgcctggg aagaagctgt     120
aggggaacaa aagatgcctt agaatggctg atgggtaagt tctacatgag aaaggaggtt     180
taaattcctc tttcccctaa atgtaaaaca aacctgcctt catcctctga agcgggagac     240
cggaaacact tttgcagtgc tagagaaatg agaatattct gactgatttg gtggggaggg     300
gggttggggg ggtgtgttcc agccctagat ataacacctc ataaacctta agacacataa     360
agtagaaatg aaaggaaaac cccgcttgct tcatccctct gaagtgcttg ctggtgtctt     420
agtattattc acaaggtttt gctgctcaag ttatttggct gtcctcaaag cgcaatattc     480
cctgatgcct cttgagagaa aagttcccta agtccgaagc atgagtcact tcgctcagtt     540
ttgatgagta atctcaggtg tcactgaacc ttgttcggaa gaagagggga gggggcgtc     600
agatttgcag acggaagaaa acaggtctct ctggattgga tggcgagacc tcgacttccc     660
taaaattgcg tcatttcgaa cccaatttgg tccagatgtt atggactccg acgggttacc     720
gtctcggaaa ctctatcacg caagcaaaag gcgaggggc ggctaattaa atattgagca     780
gaaagtcgcg tggggagagt gtcacgtggc tctccaggct catcacgcct gagataaata     840
aggcgaagca ggagcaggga ctagagcgca ctcggaccag ctccactcca gcaccgcggc     900
ggaggagagc gaggagcgcc cagcaagtgc gcacctgcgg agcatcaccg ggtcc          955
```

<210> SEQ ID NO 2
<211> LENGTH: 727
<212> TYPE: DNA
<213> ORGANISM: Mus musculus

<400> SEQUENCE: 2

```
cggagaacat ttttgtttca gcatttcatc tgaagccacg gtttcacatc atcaagtctg      60
caaaaaaccg ttcacaaacc acaccaaaac ttctcggtaa agaactccta aggccaaaga     120
gggagactgg gtagattgtt tttaatttgt ttcttttttgt caaggggga caaacacgct     180
ttggtgagtg cgagtgttta ttctgggaca caaacccaga gtctggaagg gagcattcaa     240
cgggtgctgc tctgccacgc aggggcagcg gtgggactca gcccatcctg ctaaggacgg     300
gcagcctgag ccaggcttgg gagtctgtca tggctgccaa aggaatcatt atctaattgc     360
agccttttct cttccttagg tttcagcagg tcccgagaga gcatttaaaa tcacatttac     420
tactttacat ctaatcacac ataagcctct ccctataccc tccaccctcc ttccattcag     480
agtgtacttt ctggagcacc atccagcaag ctgggtggaa ctcgtgacgg gaaatggaaa     540
cggcacccac gaaggcgtga ttccttgtag atccttgagt gacggacggg tgaggtttcc     600
gtcaggcaag cccagccacc ttcgtggagg agccccggac aagtgtaagt ttcgcagagc     660
```

```
tggtctccag cttacttctg ctaatgctac cccaggcctt tagacggaga acagatggca    720
gatggag                                                              727
```

<210> SEQ ID NO 3
<211> LENGTH: 819
<212> TYPE: DNA
<213> ORGANISM: Rattus norvegicus

<400> SEQUENCE: 3

```
ttgagaacat ttttgtctca gcatttcatc tgaagctatg gttttacatc accaagtctg     60
caaaaaacag ttcgcaaacg gaaccaaaac ttttcgaca aagaactttt aaggcgaaaa    120
cgggagatag agtagattgt ttttaatttg tttctttctg gcaaggggg acaaaacaca    180 ctttgacgag tgtgagtgtt tattctggga caaacccaga gtatgaaagg gagcattcgg    240
tgggtgccgc tctgccatgc aggggcgcgg tggggctcag cccatcctgc tcaggaccca    300
gcctggcccc aggcttggga gtctgtcatg gctgccagag gaatcattat ctaattgcag    360 cctttctct tccttaggtt tcagcgcgtc ccaggagagc atttaaaatc acatttacta    420
ctttaccatc taatcacaca taagcctctc ccatacccatc caccctcctt ccattcagag    480
tgtactttct ggagcgccat ccagcaagct gggtggaatt cgtgacggga aatggaaacg    540
gtacccacga aggcgtgatt cctcgtagct ccctgagtga ggttcccatc aggcaagccc    600
ggccaccttc gtggagaagc gcggacaagt gtaagttttg cagagctggg gtctctagct    660
tgcttctgct aatgctaccc caggccttta gacagagaac agatggcaga tggagttctct    720 tattgccatg cgcaaacgct gagcccacct catgatcccg gaccccatgg ttttcagtag    780
acaacctggg ctaagaagag atctccgacc ttatagagc                           819
```

<210> SEQ ID NO 4
<211> LENGTH: 834
<212> TYPE: DNA
<213> ORGANISM: Homo sapiens

<400> SEQUENCE: 4

```
ttttttttt tttgtaatt tcatttcaaa ctattatttt ataagacctg gcctattact     60
gagtatgcag gcagaatatg aaaattactc caaaactttt ttaaatgaaa ttttcaagat    120
gcaaaaagtg aaactttaaa atttcagtgg aagaagggga acaaaaacat tttaataaat    180
gagagtgttt attccagaat gggaatatag agacaaggaa ggtaccatgt gaatgggtgc    240
acctcgctct ctggggtcaa tgataggaaa cagcctgtcc cacagtcaag gcagccttgc    300
ccaggctatg agtctattgt ggatgctggg gcattgttat ctaagtgcag cctcttttgct    360 tcctcaggtt tcagcatttc ccatgagatc atttaaaatc acatttgcta ttttaccatc    420
taatcacaca taagcctctc cccacactcc ccccgccctg tttccatcca aggagtgcac    480
tttctggagc accagcaacc agggtggaac tcgtgacggg aaatgggaat ggcacccaag    540
aaagcatgat ttctgtagtt tcgtgaatga tagcaaggct cccatcagac aagctgagcc    600
actgtcactg aggaggacaa acgagtgcaa gtctttgcaa agcttggcat ctcagacttg    660
cctctcattt cttgcttcac acactagcct cttggctaga aacagacat cagatggagt    720 ttcttctggc tatgcctgaa tgttaagctg aacgtatgtt ccaggagctc gtggtctcca    780
gtagaggcaa tctgggatag aagagaagat atttcttacg tagaagacaa gcaa            834
```

METHODS AND COMPOSITIONS FOR DECREASING CHRONIC PAIN

CROSS-REFERENCE

This application is a continuation of U.S. non-provisional patent application Ser. No. 13/637,977, which was filed Sep. 27, 2012, a national stage entrant of international patent application PCT/US2011/31297 under 37 U.S.C. § 371, which was filed Apr. 5, 2011, and which claimed the priority of U.S. Patent Application Ser. No. 61/321,117, which was filed Apr. 5, 2010, all of which applications are incorporated herein by reference in their entireties.

STATEMENT AS TO FEDERALLY SPONSORED RESEARCH

This invention was made with government support under a Phase I SBIR awarded by National Institute of Neurological Diseases and Stroke of the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 25, 2020, is named SEQID.txt and is 4.9 kb in size.

BACKGROUND OF THE INVENTION

Traumatic and non-traumatic injuries, nerve lesion, amputation, diabetes, HIV/AIDS, alcoholism, and nerve compression are frequently accompanied by debilitating chronic pain, which can result in reduced quality of life and productivity. Current treatments involve pharmacological, surgical, electrical stimulation, and physical rehabilitation therapy. A major challenge facing these approaches is a general failure to target pain pathways selectively, resulting in undesired side effects, such as central nervous system depression that may impair physical and mental ability. More invasive approaches such as surgery and electrical stimulation also modulate pain pathways with poor specificity. There is a need in the art for selective methods of targeting signaling pathways for treatment of pain, with minimal invasiveness.

SUMMARY OF THE INVENTION

The present invention provides compositions and methods for the selective silencing of neurons in pain pathway by using a combination of inhibitory light-sensitive protein gene transfer and wavelength specific illumination.

In one aspect, the present invention provides a recombinant nucleic acid, comprising: a nucleic acid fragment encoding a light-sensitive protein; and a regulatory nucleic acid fragment that is capable of directing selective expression of said light-sensitive protein in a cell of the central nervous system (CNS). In some embodiments, the light-sensitive protein is sensitive to a light that is a visible light or a light that is delivered transdermally. In some embodiments, the light-sensitive protein is capable of modulate the neuronal activity of the cell of the CNS. In some embodiments, the neuronal activity of the cell is associated with pain transmission or generation.

In some embodiments, the light-sensitive protein is a membrane bound microbial opsin. In some embodiments, the microbial opsin is a photosensitive ion channel or pump. In some embodiments, the light-sensitive protein is selected from the group consisting of: halorhodopsin (NpHR), enhanced halorhopopsin (eNpHR), archaerhodopsin-3 (Arch), *Leptosphaeria maculans* (Mac), and functional variants thereof.

In some embodiments, the cell is associated with pain neurotransmission and/or generation, such as a Wide Dynamic Range (WDR) cell, a cell of dorsal root ganglia (DRG), or a cell of NK-1 Expressing Afferent Fibers. In some embodiments, the cell is a nociceptive neuron of the DRG. In some embodiments, the regulatory nucleic acid fragment has the sequence of a promoter that is specific to the cell of the CNS. In some embodiments, the promoter is preprotachykinin-A (PPT) promoter, or voltage-gated sodium channel subunit alpha (Scn10a) promoter.

In another aspect, the present invention provides a recombinant virus, comprising a recombinant nucleic acids disclosed herein. In some embodiments, the virus is selected from the group consisting of: recombinant adeno-associated virus (AAV), recombinant retrovirus, recombinant lentivirus, and recombinant poxvirus. In some embodiments, the virus is an AAV virus of a serotype selected from the group consisting of: AAV1, AAV2, AAV3, AAV4, AAV5, AAV6, AAV7, AAV8, AAV9, AAV10, AAV11, AAV12, and hybrids thereof. In some embodiments, the virus is sc-rAAV1 or sc-rAAV8.

In another aspect, the present invention provides a host cell, derived from a cell transfected with a recombinant virus provided herein.

In another aspect, the present invention provides a vector, comprising a recombinant nucleic acid provided herein, as well a host cell, derived from a cell transfected with the vector.

In another aspect, the present invention provides a host cell, comprising a recombinant nucleic acids provided herein.

In another aspect, the present invention provides a method to relieve neuropathic pain, comprising: optically silencing pain-associated neurotransmission or generation in a mammalian subject in need of such relief. In some embodiments, the method comprises: expressing in a cell of the subject the recombinant nucleic acid provided herein; and controlling the neural activity of the cell with a light beam to modulate the expression of the light-sensitive protein, thereby relieve the neuropathic pain in said subject. In some embodiments, the controlling is carried out with high spatial and temporal precision using a specifically positioned device where the light emission is controlled over time. In some embodiments, the extent of said silencing is dynamically controlled via a variable intensity optical source with temporal control. In some embodiments, the optical source comprises an implantable 1- or 2- or 3-dimensional fiber optic device.

In some embodiments, the method provides significant analgesia for chronic neuropathic pain without off-target effects. In some embodiments, the off-target effects comprise general central nervous system depression. In some embodiments, the analgesia results in greater than 1, 5, 10, 15, 20, 30, 40, 50, 60, 70, 80, 90 percent reduction in said neuropathic pain.

In yet another aspect, the present invention provides a method of optically controlling neural activity in a cell, comprising: expressing in a cell a recombinant nucleic acid provided herein; and controlling the neural activity of said cell with a light beam to modulate the expression of said light-sensitive protein.

In another aspect, the present invention provides a method of optically control neural activity in a subject, comprising: expressing in a cell of a subject one of the recombinant nucleic acids provided herein; and controlling the neural activity of the cell with a light beam to modulate the expression of the light-sensitive protein.

In another aspect, the present invention provides a pharmaceutical composition, comprising a recombinant nucleic acids provided herein and a pharmaceutically acceptable excipient.

In another aspect, the present invention provides kit, comprising a recombinant nucleic acids provide herein.

In another aspect, the present invention provides a kit, comprising a recombinant viruses provided herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 9 depicts spinal column anatomy (above) and DRG neuron cultures (below). DRG neuron cultures were used in the testing of AAV vectors and transcription regulatory units according to some embodiments of the invention.

FIG. 10 depicts the sequence of the rat proximal PPTA promoter fragment spanning −865+92 base pairs (SEQ ID NO: 1).

FIG. 11 depicts the promoter region and mouse (SEQ ID NO: 2)-rat (SEQ ID NO: 3)-human (SEQ ID NO: 4) alignment for the voltage gated sodium channel (Scn10a) promoter. A variety of transcription factor binding sites are highlighted and conserved among these three species.

DETAILED DESCRIPTION OF THE INVENTION

I. General Overview

Figure 1:
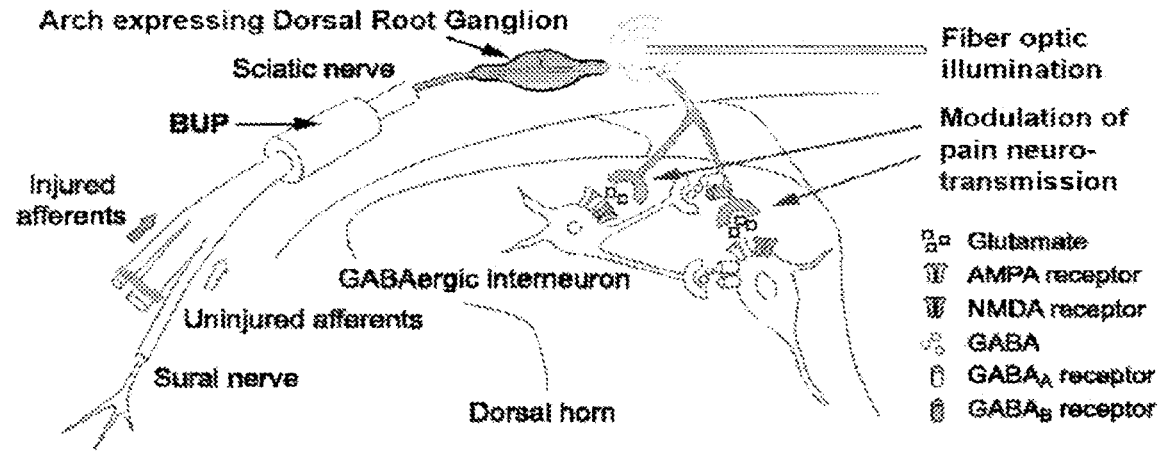
FIG. 1 depicts one exemplary embodiment where neurons in the Dorsal Root Ganglion (DRG) expresses the AAV delivered optical silencer Archaeorhodopsin (Arch) shown in gray silences pain-associated neurotransmission or generation via optical hyperpolarization with illumination.

The present invention provides compositions and methods for the selective silencing of neurons in pain pathway by using a combination of inhibitory light-sensitive protein gene transfer and wavelength specific illumination.

Embodiments of the present disclosure pertain to light-sensitive proteins, a class of proteins that exhibit a response to light. Induction by light can modulate one or more of various attributes of light-sensitive proteins including, but not limited to, cellular localization or distribution, structural conformation, membrane translocation, half-life, stability, post-translational modification, and interaction with other proteins or with nucleic acids. These light-induced changes can influence the signaling function of a light-sensitive protein, which may in turn alter the behavior of a cell.

Exemplary alterations of cell behavior include, but are not limited to, apoptosis, necrosis, up-regulation of certain genes, down-regulation of certain genes, secretion of cytokines, alteration of cytokine receptor responses, regulation of cytochrome c oxidase and flavoproteins, activation of mitochondria, stimulation antioxidant protective pathway, modulation of cell growth and division, alteration of firing pattern of nerves, alteration of redox properties, generation of reactive oxygen species, modulation of the activity, quantity, or number of intracellular components in a cell, modulation of the activity, quantity, or number of extracellular components produced by, excreted by, or associated with a cell, or a combination thereof.

II. Cell Specific Expression of Light-Sensitive Proteins

In one aspect, the present invention provides a recombinant nucleic acid, comprising: a nucleic acid fragment encoding a light-sensitive protein; and a regulatory nucleic acid fragment that is capable of directing selective expression of said light-sensitive protein in a cell of the central nervous system (CNS).

A. Light-Sensitive Proteins and Variants

In some embodiments, the present disclosure relates to light-sensitive proteins.

By "light-sensitive protein" herein is meant a protein that is responsive to light. Membrane light-sensitive proteins can be activated with light, which leads to either a cation or anion exchange across the membrane that leads to either a hyperpolarization or depolarization of the membrane. In other words, depending on which protein is introduced and expressed, neural tissue can be either excited or depressed with light stimulation. Light-sensitive proteins include but are not limited to any membrane bound light-sensitive ion channel or proton pump that leads to a hyperpolarization or depolarization of the cell as a function of light stimulation.

Light-sensitive proteins include, but are not limited to, opsins such as rhodopsin, blue opsin, red opsin, halorhodopsin (NpHR), channelrhodopsin-2, enhanced halorhodopsin (eNpHR), archaerhodopsin-3 (Arch), *Leptosphaeria maculans* (Mac) and functional fragments or variants thereof. Light-sensitive opsins of the present invention also include light-sensitive ion channels and ion pumps. In some cases, a combination of two or more light-sensitive proteins are used in the same method.

Light-sensitive proteins may also include proteins that are at least about 60%, at least about 70%, at least about 80%, at least about 90%, at least about 95%, or at least about 99% identical to the light-sensitive proteins such as rhodopsin, blue opsin, red opsin, halorhodopsin (NpHR), enhanced halorhopopsin (eNpHR), archaerhodopsin-3 (Arch), *Leptosphaeria maculans* (Mac). Preferably, these variants retain the function of the parent protein, such the sensitivity to light and the ability to modulate neuronal activities as described herein.

In some embodiments, the opsins is the one disclosed in Chow, B. Y., et al. High-performance genetically targetable optical neural silencing by light-driven proton pumps. Nature 463, 98-102.

In some embodiments, the light-sensitive protein comprises the halorhodopsin (NpHR) having the sequence of Genbank no. EF474018.

In some embodiments, the light-sensitive protein comprises the enhanced halorhodopsin (eNpHR) having the sequence of Genbank no. EF474018.

In some embodiments, the light-sensitive protein comprises the archaerhodopsin-3 (Arch) having the sequence of Genbank no. GU045599.

In some embodiments, the light-sensitive protein comprises the *Leptosphaeria maculans* (Mac) having the sequence of Genbank no. GU045595.

Light-sensitive proteins of the present disclosure can be derived from any organism source including, but not limited to bacteria, viruses, fungi, mycobacteria, protozoa, molds, yeasts, plants, humans, non-humans, multi-cellular parasites, vertebrates, animals, and archeabacteria.

In some embodiments, a light-sensitive protein comprises a light sensitive extracellular domain and an intracellular domain capable of modulating an intracellular signaling pathway. The coupling of these extracellular and intracellular domains allows a light-sensitive GPCR to use light energy to activate G-proteins at the intracellular side of a cell. The intracellular regions of a GPCR determine the G protein specificity and its precisely targeted role in cellular signaling. In embodiments of the present disclosure, a selected intracellular G-protein can be recombinantly fused to the intracellular loops of a selected light-sensitive GPCR (e.g., rhodopsin) that can be activated by different wavelengths of light. In some embodiments, a selected signaling protein is fused to a selected light-sensitive protein to confer light sensitivity on one or more signaling pathways involving the signaling protein.

A light-sensitive protein may be stimulated by an energy source, such as irradiation, resonance energy transfer, exciton migration, electron injection, or chemical reaction, to an activated energy state that is capable of effecting the predetermined cellular change desired.

In some embodiments, the light-sensitive protein can be activated by one or more ranges of wavelengths of light. Typically, a light-sensitive protein responds maximally to a specific wavelength of light, with tapering levels of response on either side of the electromagnetic spectrum from the specific wavelength. In some embodiments, a light-sensitive protein is sensitive to a light that is a visible light or invisible light.

Visible light includes light with a wavelength from about 390 to 750 nm that a typical human eye will respond to, such as 380-450 nm (violet), 450-475 nm (blue), 476-495 nm (cyan), 495-570 nm (green), 570-590 nm (yellow), 590-620 nm (orange), 620-750 nm (red).

In some embodiments, the light-sensitive protein can be absorbed and/or be activated by light that is delivered transdermally. This is accomplished by the use of a transdermal device that transmits high or low frequency light to activate the subdermally-expressed light-sensitive protein.

In some embodiments, the light is delivered through a light source that is placed (e.g. by implantation) under the skin.

In some embodiments, the light-sensitive protein can be absorb and/or be activated by light with a wavelength of about 650 to about 800 nm, about 400 to about 800 nm, or a partial range (e.g., at a portion in the range) within the wavelength range of about 200 nm to about 800 nm. In some embodiments, the light-sensitive protein may have a measurable absorbance over a range having a width of at least about 50 nm, preferably 100 nm, and more preferably 150 nm within the above-described wavelength range. If these wavelength ranges having the measurable absorbance exceed about 150 nm (e.g., about 400 nm, about 600 nm, etc.), these wavelength ranges may be about 200 nm, about 250 nm, about 300 nm, about 350 nm, about 400 nm, about 450 nm, about 500 nm, about 550 nm, about 600 nm, or the like. In other embodiments, the light-sensitive protein has a measurable absorbance over a certain range at two or more (e.g., 3, 4, or the like) different positions within the wavelength range. The certain range can have a width of about 50 nm, about 100 nm, about 200 nm, about 250 nm, about 300 nm, about 350 nm, about 400 nm, or about 500 nm.

When a protein is sensitive to visible light, the light sensitivity of a protein can be described in terms of the color of the light, including red, orange, yellow, green, blue, indigo, and violet light. Thus, an opsin responding to blue light may be referred to as blue opsin, and an opsin responding to red light may be referred to as red opsin.

In some embodiments, variants of light-sensitive protein are genetically engineered to have desired properties, such as can be modulated by a light of particular wavelength of interest.

In some embodiments, the protein variants described herein rely on mutational strategies such as screening and/or selection to achieve the goals (such as optimization of desired light sensitivity discussed above). Screening involves inspection of a population for a given characteristic (usually a phenotype of interest) but placed no limits on the viability of the organisms that possessed (or more importantly did not possess) the desired characteristic. When selection is used, a predetermined mechanism allows only a certain population to survive.

In some embodiments, the genetic optimization process is performed by creating random mutations and observing the impact of these mutations on the desired properties. This process requires the screening of mutations and determining which mutants are to be used as templates for further exploration. A single random-mutation cycle yields several mutant proteins with improved properties. In other embodiments, several or more cycles are performed to achieve a significant improvement. Random mutations in most cases are more likely to be destructive or neutral than constructive.

For the random mutant studies wherein screening is involved, the process is described by L. You et al. Protein Eng. 9, 719 (1996); L. Wan et al., Proc. Natl. Acad. Sci. U.S.A. 95, 12825-12831 (1998); M. Callahan et al., Methods Mol. Biol. 57, 375-385 (1996). The net result is a population of mutant proteins with no a priori bias of location in the sequence. Alternatively, a combination of methods is used to generate controlled numbers of randomly distributed mutations.

In some embodiments, semi-random mutagenesis is performed wherein site directed and random mutagenesis are combined to achieve high mutagenesis efficiencies over a limited region. See J. U. Bowie et al. Science. 247, 1306-1310, (1990); J. Wen, et al., Nat. Struct. Biol. 3, 141-148, (1996); M. P. Krebs et al., J. Mol. Biol. 267, 172-183, (1997); M. P. Krebs et al., Proc. Natl. Acad. Sci. U.S.A. 90, 1987-1991, (1993); and S. R. Whaley et al., Nature. 405, 665-668, (2000).

In some embodiments, directed evolution and combinatorial methods are used. In these embodiments, one begins with wild-type protein that has become efficient for its intended purpose through evolution. A key challenge in using directed evolution for materials optimization is establishing a selection method that focuses on the desired properties of the material generated by the host. The use of directed evolution may not guarantee the creation of the ultimate material because the number of possible mutations and the time it takes to explore all the possibilities is years if not decades long. But directed evolution does provide a method of exploring a large number of possible mutations in a systematic way which yields the highest probability of improving the properties of a biological material.

The extent to which the variation in a population increases is dictated by the choice of the mutagenesis method. Site-directed mutagenesis can be used to explore small changes by changing one residue, and in the absence of structural information about the protein, can be used to fine-tune a particular mutant. However, there are instances wherein the modification of one amino acid provides greatly superior advantages to the un-mutated construct.

In some embodiments, other techniques can be used that may be designed to explore a greater area of the mutational landscape for a given protein. For example, the semi-random mutagenesis technique samples a mutational space that is greater compared to site-directed mutagenesis. The sampling of this space means that a new optimum might be reached instead of continuing to improve an original optimization (as in site directed mutagenesis). In this regard, random mutagenesis presents simultaneous advantages and disadvantages: it can be used to find new regions in the protein for optimization, but at the cost of neglecting the original optimization unless randomized libraries incorporating the desired mutation are used. The strategies for optimizing photochemical properties generally should take into account the localized nature of the mutational landscape. However, once key regions for mutagenesis are discovered, semi-random mutagenesis or site directed mutagenesis provides the most productive approach.

B. Targeting Specific Tissue and/or Cell Types

In another aspect, the present invention provides compositions and methods for the specific delivery of light-sensitive proteins to sensory neurons in the CNS to optically silence pain-associated neurotransmission, resulting in reduced sensation of chronic pain (FIG. 1).

In some embodiments, the light-sensitivity of proteins or protein domains is employed in the modulation of neuronal activity of a cell. Recombinant light-sensitive opsins can be engineered to inhibit signaling of pain pathways. In some embodiments, such inhibitory opsin constructs are genetically targeted and stably expressed in desired cell populations to optically silence pain-associated neurotransmission or generation. In some embodiments, delivery of optical neural silencers can provide significant analgesia for chronic neuropathic pain without off-target effects such as general central nervous system depression. In some embodiments, such analgesia results in greater than 1, 5, 10, 15, 20, 30, 40, 50, 60, 70, 80, 90 percent reduction in neuropathic pain. When expressed in mammalian neurons, these optical neuromodulators enable the complete control of neural activity with extremely high spatial and temporal precision.

Embodiments of the disclosure relate to a cell associated with pain neurotransmission or generation. Some embodiments of the invention involve targeting a cell of the central nervous system (CNS). Cells of the invention can include, but are not limited to, wide dynamic range (WDR) cells, cells of dorsal root ganglia (DRG), nociceptive neurons of the DRG, and cells of NK-1 Expressing Afferent Fibers.

In some embodiments, the cell to be target is a DRG cells, including the C-fiber and A-delta/A-beta cells. The A fibers act to inhibit secondary DRG cells in pain transduction.

A dorsal root ganglion (or spinal ganglion) is a nodule on a dorsal root that contains cell bodies of neurons in afferent spinal nerves.

In mammals, nociceptive neurons or nociceptors are sensory neurons that are found in any area of the body that can sense pain either externally or internally. External examples are in tissues such as skin (cutaneous nociceptors), cornea and mucosa. Internal nociceptors are in a variety of organs, such as the muscle, joint, bladder, gut and continuing along the digestive tract. The cell bodies of these neurons are located in either the dorsal root ganglia or the trigeminal ganglia. The trigeminal ganglia are specialized nerves for the face, whereas the dorsal root ganglia associate with the rest of the body. The axons extend into the peripheral nervous system and terminate in branches to form receptive fields.

The wide dynamic range (WDR) or "convergent" neuron is the most populous type of those neurons whose cell bodies are located in the dorsal horn of the spinal cord. WDR neurons are responsive to all sensory modalities (thermal, chemical and mechanical) and a broad range of intensity of stimulation from peripheral nerves. They steadily increase their firing rate as the stimulus intensity rises into the noxious range. There are, for example, wide dynamic range neurons that respond to benign stroking as well as to painful heat and intense mechanical damage at the cell's receptive field. Dorsal horn neurons that receive input from the viscera via thin afferent fibers are all WDR type.

NK-1 Expressing Afferent Fibers are another potential therapeutic target. Hyperactivity of NK-1 expressing cells occurs as a function of peripheral nerve damage and the threshold of response to noxious stimulus is decreased (i.e., hypersensitivity to noxious or painful stimuli).

For targeting specificity, some embodiments involve two previously identified DRG specific promoters, PTT and Scn10a, as well as the strong ubiquitous CMV promoter. In some embodiments, for neural silencing enhanced halorhodopsin (eNpHR) is employed as well as a newly identified and more sensitive proton pump (ARCH) derived from *Halorubrum sodomense* that enables near-100% silencing of mouse cortical neurons.

Some embodiments of the present invention relate to tissue or cell type-specific expression of a recombinant nucleic acid. CNS-specific expression can be achieved through the use of CNS-specific promoter. Promoters with useful specificity for the present disclosure include, but are not limited to preprotachykinin-A (PPT) promoter, voltage-gated sodium channel subunit alpha (Scn10a) promoter.

Preprotachykinin-A (PPT) promoter directs high levels of expression in dorsal root ganglia (DRG) neurons in culture either endogenously or when linked to a receptor construct. Morrison C F et al., Mol Cell Neurosci. 1994, 5(2):165-75. FIG. 10 depicts the sequence of the rat proximal PPTA promoter fragment spanning −865+92 base pairs. The positions of transcription factor binding sites are shown (underlined). The proximal rtPPT-A promoter contains a number of transcription factor binding sites including E boxes, an NRSE, CRE or AP1 binding elements, AP2/SP1 binding elements, octamer binding elements and a complex binding element that can bind a number of single and double stranded transcription factors. The E box located between −60 and −55 is shown highlighted in grey. This sequence corresponds to bases 2494-3448 from GI:294623.

FIG. 11 depicts the promoter region and mouse-rat-human alignment for the voltage gated sodium channel (Scn10a) promoter. A variety of transcription factor binding sites are highlighted and conserved among these three species.

In some embodiments, the regulatory sequence is a full length cell-specific promoter (e.g. PPT or Scn10a), a functional variant of the cell-specific promoter (e.g. PPT or Scn10a promoter), which has one or more mutations but retain the function of the parent promoter, or a functional fragment of the parent promoter.

In some embodiments, the promoters are of a human origin.

In some embodiments, the regulatory sequence comprises one or more inducible promoters such that the expression of the light-sensitive protein is controlled via such promoters.

In some embodiments, the cell specific targeting is carried out using a delivery vehicle comprising a cell-specific ligand that can recognize the target cell specifically, for example, via cell specific receptor-ligand pair, or antibodies against cell specific surface antigens. Such cell specific targeting method can be carried independently or in combination with the cell specific promoter targeting method provided herein.

In some embodiments, the cell specific targeting is carried out using a delivery no-viral delivery systems that comprise nanoparticles (e.g. liposomes).

C. Recombinant Viruses

In another aspect, the light-sensitive proteins are expressed in the cells using gene therapy. The gene therapy uses a vector including a nucleotide encoding the light-sensitive protein. A vector (sometimes also referred to as gene delivery or gene transfer vehicle) refers to a macromolecule or complex of molecules comprising a polynucleotide to be delivered to the cell. The polynucleotide to be delivered may comprise a coding sequence of interest in gene therapy. Vectors include, for example, viral vectors such as adenoviruses, adeno-associated viruses (AAV), and retroviruses, liposomes and other lipid-containing complexes, and other macromolecular complexes capable of mediating delivery of a polynucleotide to a target cell. Some embodiments of the present disclosure involve a vector comprising a recombinant nucleic acid.

In some embodiments, the present invention provides a recombinant virus comprising a recombinant nucleic acid of the invention. A recombinant virus can be an adeno-associated virus (AAV), recombinant retrovirus, recombinant lentivirus, or recombinant poxvirus. In some embodiments, the virus is an AAV selected from the group consisting of: AAV1, AAV2, AAV3, AAV4, AAV5, AAV6, AAV7, AAV8, AAV9, AAV10, AAV11, AAV12, and hybrids thereof. In some embodiments, sc-rAAV1 or sc-rAAV8 is used.

In some embodiments, a self-complementary vector (sc) is used, which includes sc-rAAV1 and sc-rAAV8. The self-complementary AAV vectors bypass the requirement for viral second-strand DNA synthesis and lead to greater rate of expression of the transgene protein, Wu, Hum Gene Ther. 2007, 18(2):171-82.

In some embodiments, several AAV vectors are generated to enable selection of the most optimal serotype, promoter, and transgene. In some embodiments, AAV vectors are packaged with both the naturally occurring serotype-8 capsid, as well as a novel tyrosine mutant AAV8 (Y733F), that have been demonstrated to give higher neuronal transduction levels.

Vectors can comprise components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities.

Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., Lupton, S., WO 92/08796, published May 29, 1992; and Lupton, S., WO 94/28143, published Dec. 8, 1994). Such marker genes can provide an added measure of control that can be advantageous in gene therapy contexts. A large variety of such vectors are known in the art and are generally available.

Vectors for use in the present invention include viral vectors, lipid based vectors and other non-viral vectors that are capable of delivering a nucleotide according to the present invention to the target cells. The vector can be a targeted vector, especially a targeted vector that preferentially binds to neoplastic cells, such as cancer cells or tumor cells. Viral vectors for use in the invention can include those that exhibit low toxicity to a target cell and induce production of therapeutically useful quantities of the light-sensitive transmembrane protein in a cell specific manner.

Examples of viral vectors are those derived from adenovirus (Ad) or adeno-associated virus (AAV). Both human and non-human viral vectors can be used and the recombinant viral vector can be replication-defective in humans.

Where the vector is an adenovirus, the vector can comprise a polynucleotide having a promoter operably linked to a gene encoding the light-sensitive transmembrane protein and is replication-defective in humans.

Other viral vectors that can be use in accordance with the present invention include herpes simplex virus (HSV)-based vectors. HSV vectors deleted of one or more immediate early genes (IE) are advantageous because they are generally non-cytotoxic, persist in a state similar to latency in the target cell, and afford efficient target cell transduction. Recombinant HSV vectors can incorporate approximately 30 kb of heterologous nucleic acid.

Retroviruses, such as C-type retroviruses and lentiviruses, might also be used in the invention. For example, retroviral vectors may be based on murine leukemia virus (MLV). See, e.g., Hu and Pathak, Pharmacol. Rev. 52:493511, 2000 and Fong et al., Crit. Rev. Ther. Drug Carrier Syst. 17:1-60, 2000. MLV-based vectors may contain up to 8 kb of heterologous (therapeutic) DNA in place of the viral genes. The heterologous DNA may include a tissue-specific promoter and a light-sensitive transmembrane protein nucleic acid. In methods of delivery to neoplastic cells, it may also encode a ligand to a tissue specific receptor.

Additional retroviral vectors that might be used are replication-defective lentivirus-based vectors, including human immunodeficiency (HIV)-based vectors. See, e.g., Vigna and Naldini, J. Gene Med. 5:308-316, 2000 and Miyoshi et al., J. Virol. 72:8150-8157, 1998. Lentiviral vectors are advantageous in that they are capable of infecting both actively dividing and non-dividing cells. They are also highly efficient at transducing human epithelial cells.

Lentiviral vectors for use in the invention may be derived from human and non-human (including SIV) lentiviruses. Examples of lentiviral vectors include nucleic acid sequences required for vector propagation as well as a tissue-specific promoter operably linked to a light-sensitive trans-membrane protein gene. These former may include the viral LIRs, a primer binding site, a polypurine tract, aft sites, and an encapsidation site.

A lentiviral vector may be packaged into any suitable lentiviral capsid. The substitution of one particle protein with another from a different virus is referred to as "pseudotyping". The vector capsid may contain viral envelope proteins from other viruses, including murine leukemia virus (MLV) or vesicular stomatitis virus (VSV). The use of the VSV G-protein yields a high vector titer and results in greater stability of the vector virus particles.

Alphavirus-based vectors, such as those made from semliki forest virus (SFV) and sindbis virus (SIN), may also be used in the invention. Use of alphaviruses is described in Lundstrom, K., Intervirology 43:247-257, 2000 and Perri et al., Journal of Virology 74:9802-9807, 2000.

Recombinant, replication-defective alphavirus vectors are advantageous because they are capable of high-level heterologous (therapeutic) gene expression, and can infect a wide target cell range. Alphavirus replicons may be targeted to specific cell types by displaying on their virion surface a functional heterologous ligand or binding domain that would allow selective binding to target cells expressing a cognate binding partner. Alphavirus replicons may establish latency, and therefore long-term heterologous nucleic acid expression in a target cell. The replicons may also exhibit transient heterologous nucleic acid expression in the target cell.

In many of the viral vectors compatible with methods of the invention, more than one promoter can be included in the vector to allow more than one heterologous gene to be expressed by the vector. Further, the vector can comprise a sequence which encodes a signal peptide or other moiety which facilitates expression of the light-sensitive transmembrane protein from the target cell.

To combine advantageous properties of two viral vector systems, hybrid viral vectors may be used to deliver a nucleic acid encoding a light-sensitive transmembrane protein to a target tissue. Standard techniques for the construction of hybrid vectors are well-known to those skilled in the art. Such techniques can be found, for example, in Sambrook, et al., In Molecular Cloning: A laboratory manual. Cold Spring Harbor, N.Y. or any number of laboratory manuals that discuss recombinant DNA technology. Double-stranded AAV genomes in adenoviral capsids containing a combination of AAV and adenoviral ITRs may be used to transduce cells. In another variation, an AAV vector may be placed into a "gutless", "helper-dependent" or "high-capacity" adenoviral vector. Adenovirus/AAV hybrid vectors are discussed in Lieber et al., J. Virol. 73:9314-9324, 1999. Retrovirus/adenovirus hybrid vectors are discussed in Zheng et al., Nature Biotechnol. 18:176-186, 2000.

Retroviral genomes contained within an adenovirus may integrate within the target cell genome and effect stable gene expression.

Other nucleotide sequence elements, which facilitate expression of the light-sensitive protein gene and cloning of the vector are further contemplated. For example, the presence of enhancers upstream of the promoter or terminators downstream of the coding region, for example, can facilitate expression.

Other embodiments of the disclosure provide for a host cell derived from a cell transfected with a recombinant virus. Still other embodiments involve a host cell comprising a recombinant nucleic acid.

In some embodiments, the DNA being packaged is self-complementary. In some embodiments, the DNA being packaged is single-stranded DNA.

D. Methods of Cell-Based and Animal-Based Testing

In another aspect, the present invention provides cell based assays and animal models to test the recombinant nucleic acids and viruses.

In some embodiments, the constructs are tagged with eGFP to enable the visualization of transduced neurons for anatomical and physiological studies. In some embodiments, the targeting specificity and transgene expression efficiency in DRG neurons are evaluated using confocal imaging and immunohistochemistry. Cell-attached and whole-cell patch clamp electrophysiology on whole mount DRG neurons may be performed using temporally patterned light stimuli to evaluate silencing efficacy, threshold sensitivity, response kinetics, and cellular toxicity of these opsins. After demonstrating efficacy of cell specific in vivo transduction and in vitro silencing, in vivo efficacy can be examined using rodent models of neuropathic pain.

III. Pain Circuits and Pathways

In one aspect, the present invention provide compositions and methods for the interference with the pain circuit and pathways to relieve pain. In some methods, such as deep brain stimulation, high frequency stimulation is used to over-stimulate an area of the nervous system, such that the area is shut down or inactivated.

Figure 4:
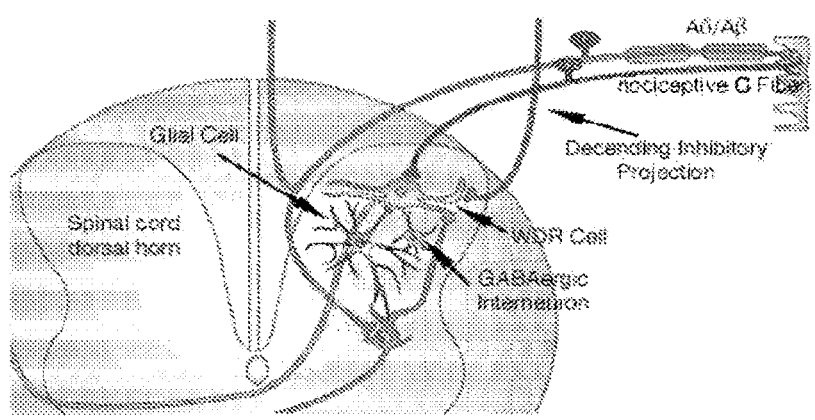
FIG. 4 depicts pain neurotransmission in the dorsal horn of the spinal cord. Wide dynamic range (WDR) neurons receive direct nociceptive excitatory and GABAergic inhibitory input prior to transmitting pain sensation downstream. Baron, R. *Nat Clin Pract Neurol* 2, 95-106 (2006); Christensen, B. N. & Perl, *J Neurophysiol* 33, 293-307 (1970).

The perception of pain following nerve injury is complex, but follows a fairly well characterized pathway from nociceptive C fibers, which synapse onto wide dynamic range (WDR) cells in the dorsal horn of the spinal cord. These WDR neurons are modulated by input from Aδ/Aβ and GABAergic inhibitory neurons before communicating to postsynaptic partners (FIG. 4).

A. Cellular Components of Pain

Within the spinal cord dorsal horn, a primary site of somatosensory processing, two classes of neurons have been implicated in the encoding of nociceptive information. The predominant nociceptive neuron in the superficial dorsal horn (laminae 1-11) is the nociceptive-specific (NS) cell, a class of neuron that is unresponsive to gentle cutaneous stimulation, has a relatively high mechanical threshold for activation, and responds optimally to stimuli sufficient to produce pain. Christensen, B. N. & Perl, E. R., *J Neurophysiol* 33, 293-307 (1970). In contrast, the deep dorsal horn (laminae V-VI) contains mainly wide dynamic range (WDR) neurons, a class of neuron that responds differentially to gentle innocuous and noxious stimuli. Mendell, L. M., Exp Neurol 16, 316-332 (1966). Both classes of neurons project to brain regions important in nociceptive processing. To date, most knowledge about the function of these cells in sensory-discriminative and affective dimensions of nociception, has been deduced from electrophysiological recordings of their responses to brief nociceptive and innocuous stimulation. Gracely, R. H., et al., Int Dent J 28, 52-65 (1978); Melzack, R. & Eisenberg, H., Science 159, 445-447 (1968).

Figure 5:
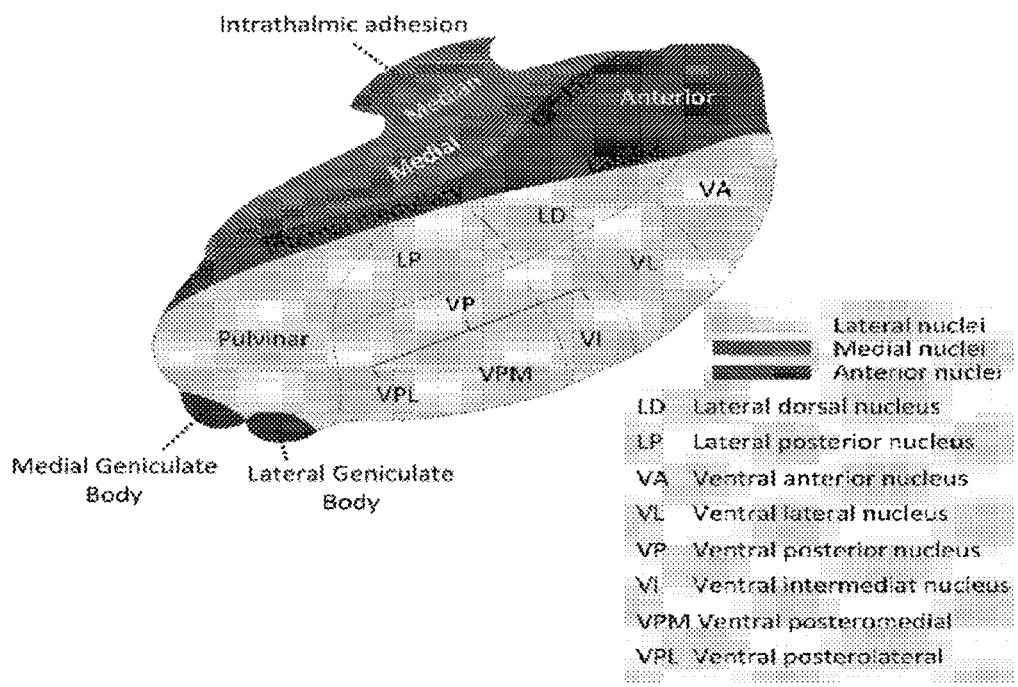
FIG. 5 depicts Wide Dynamic Range (WDR) cells are second order interneurons in the dorsal horn, projecting to the spinothalamic tract and ultimately to the Ventro Posterolateral Nucleus (VPN) in the thalamus. Together with the Ventral Posteromedial Nucleus (VPM) it constitutes the ventral posterior nucleus.

C-fibers are the primary afferents, which synapse onto WDR cells directly (and also GABAergic interneurons). WDR cells become hyperexcitable following injury by a variety of mechanisms, which is linked to glutamate-mediated death of GABAergic interneurons. Wide Dynamic Range (WDR) cells are second order interneurons, projecting to the spinothalamic tract and ultimately to the Ventro Posterolateral Nucleus (VPN) in the thalamus (FIG. 5). Together with the Ventral Posteromedial Nucleus (VPM) it constitutes the ventral posterior nucleus. The VPN projects to the postcentral gyrus (Brodmann's Areas 3,1,2) and receives information from the spinothalamic tract and the medial lemniscus of the posterior column-medial lemniscus pathway. WDR cells survive in afferent injury situations, resulting in hyperexcitability. GABAergic Interneurons are the local inhibitory cell in the dorsal horn and provide inhibition of WDR cells. Following injury, these interneurons either die or survive with reduced GABA production.

B. Physiological Changes Associated with Nerve Injury

Ectopic activity of primary afferents increases for ~8 weeks following injury, then decreases. Scholz, J., et al., *J Neurosci* 25, 7317-7323 (2005). This circuit remains hyperactive, and is accompanied by central sensitization in the dorsal horn. Scholz, J., et al., *J Neurosci* 25, 7317-7323 (2005); Moore, K. A., et al., *J Neurosci* 22, 6724-6731 (2002), and sprouting of central terminals of large myelinated primary afferents. These sprouted central terminals contain substance P (SP) and form pericellular baskets around DRG neurons. Zhang, H., et al., *J Neurosci* 27, 12067-12077 (2007). Injury-induced loss of inhibition within spinal cord, Moore, K. A., et al., *J Neurosci* 22, 6724-6731 (2002), results from diminished presynaptic inhibition at central terminals of low-threshold myelinated fibers. Inhibition is reduced in both frequency and amplitude due to apoptosis of ~25% of GABAergic interneurons. Scholz, J., et al., *J Neurosci* 25, 7317-7323 (2005). However, GABA levels drop by disproportionate amounts, suggesting limited functioning of surviving interneurons. Furthermore, there is diminished A-fiber mediated inhibition of C-fiber-evoked responses in dorsal horn neurons resulting in reduced GABA levels and reduction in spontaneous presynaptic release. Interestingly, this GABA decrease only occurs on the ipsilateral side. Glutamic Acid Decarboxylase 65 (GAD), but not GAD67, levels drop in all laminae of dorsal horn, and there is reduced GABA receptor expression.

C. Sequence of Events Leading to GABAergic Cell Death

Figure 6:
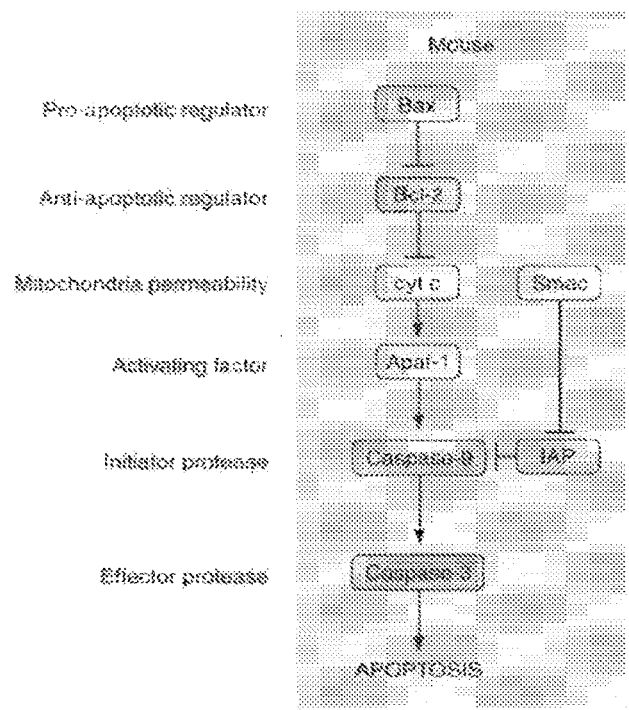
FIG. 6 depicts the apoptotic pathway in mouse.

There are a series of events leading to GABAergic Cell Death:

1. Increase in Ectopic Activity of Injured Afferents.
2. Hyperactivity is transmitted by excitatory transmitter Glutamate into dorsal horn.
    i. NMDA-gated glutamate receptor activation causes influx of Ca(2+) (calcium toxicity blocking NMDA receptor decreases apoptosis. Scholz, J., el al., *J Neurosci* 25, 7317-7323 (2005).
3. Caspase pathway triggered to induce cell death (FIG. 6).
    i. TUNEL-positive cells indicate mechanism is not necrosis, but rather apoptosis.
    ii. ~25% of inhibitory GABAergic interneurons die (n=100 for GABAergic cells, n=169 for other cells)
4. Loss of GABAergic Interneurons causes hypersensitization of local circuit in dorsal horn.
    i. GABA losses disproportionate to cell death, suggesting cells have limited functionality following injury.
    ii. Neighboring afferents may be involved in advancing this state. Scholz, J., et al., *J Neurosci* 25, 7317-7323 (2005).

In some embodiments, the stimulation provided by the light-sensitive protein itself can be neuroprotective and can protect the neuron that is stimulated. It has been known that low-threshold stimulation has a neuroprotective effect.

D. Neuropathic Pain

Embodiments of the disclosure relate to the treatment of pain associated with neuropathic pain and/or CNS dysfunction. Neuropathic pain may result from a disorder of peripheral nerve, dorsal root ganglia, spinal cord, brainstem, thalamus or cortex. Neuropathic pain may be associated with a nerve or tract injury. Pain may be chronic inflammatory pain, pain associated with arthritis, fibromyalgia, back pain, cancer-associated pain, pain associated with digestive disease, pain associated with Crohn's disease, pain associated with autoimmune disease, pain associated with endocrine disease, pain associated with diabetic neuropathy, phantom limb pain, spontaneous pain, chronic post-surgical pain, chronic temporomandibular pain, causalgia, post-herpetic neuralgia, AIDS-related pain, complex regional pain syndromes type I and II, trigeminal neuralgia, chronic back pain, pain associated with spinal cord injury or recurrent acute pain.

Neuropathic pain includes chronic pain, such as lower back pain; osteoarthritis; joint pain, e.g., knee pain or carpal tunnel syndrome; myofascial pain, and neuropathic pain. The term "pain" further includes acute pain, such as pain associated with muscle strains and sprains; tooth pain; headaches; pain associated with surgery; or pain associated with various forms of tissue injury, e.g., inflammation, infection, and ischemia.

Neuropathic pain can be related to a pain disorder, a term referring to a disease, disorder or condition associated with or caused by pain. Examples of pain disorders include arthritis, allodynia, a typical trigeminal neuralgia, trigeminal neuralgia, somatoform disorder, hypoesthesis, hypealgesia, neuralgia, neuritis, neurogenic pain, analgesia, anesthesia dolorosa, causlagia, sciatic nerve pain disorder, degenerative joint disorder, fibromyalgia, visceral disease, chronic pain disorders, migraine/headache pain, chronic fatigue syndrome, complex regional pain syndrome, neurodystrophy, plantar fasciitis or pain associated with cancer.

The term pain disorder, as used herein, also includes conditions or disorders which are secondary to disorders such as chronic pain and/orneuropathic pain, i.e., are influenced or caused by a disorder such as chronic pain and/or neuropathic pain. Examples of such conditions include, vasodialation, and hypotension; conditions which are behavioral, e.g., alcohol dependence (see, e.g., Hungund and Basavarajappa, (2000) Alcohol and Alcoholism 35:126-133); or conditions in which detrimental effect(s) are the result of separate disorders or injuries, e.g., spinal cord injuries.

Neuropathic pain can involve persistent, spontaneous pain as well as allodynia, which is a painful response to a stimulus that normally is not painful. Neuropathic pain also can be characterized by hyperalgesia, in which there is an accentuated response to a painful stimulus that usually is trivial, such as a pin prick. Unlike nociceptive pain, neuropathic pain generally is resistant to opioid therapy (Myers, supra (1995)).

The method of the invention is useful in alleviating neuropathic pain regardless of the etiology of the pain. For example, a method of the invention can be used to alleviate neuropathic pain resulting from a peripheral nerve disorder such as neuroma; nerve compression; nerve crush, nerve stretch or incomplete nerve transsection; mononeuropathy or polyneuropathy. A method of the invention also can be used to alleviate neuropathic pain resulting from a disorder such as dorsal root ganglion compression; inflammation of the spinal cord; contusion, tumor or hemisection of the spinal cord; tumors of the brainstem, thalamus or cortex; or trauma to the brainstem, thalamus or cortex.

The method of the invention can be useful, for example, to alleviate neuropathic pain resulting from a neuroma, which can develop readily after traumatic injury to nerve, especially when a whole nerve is severely crushed or transsected. In a neuroma, the neurite outgrowth that normally regenerates a peripheral nerve is aberrant or misguided due, for example, to a physical obstruction such as scar tissue. Thus, a regenerating nerve fiber is entangled in an environment in which mechanical and physical factors precipitate abnormal electrophysiologic activity and pain (Myers, supra (1995)). An amputation neuroma, for example, can cause phantom pain or can cause pain triggered by the use of a limb prosthesis. As disclosed herein, such neuropathic pain can be alleviated by administration of a prosaposin receptor agonist according to a method of the invention.

Nerve compression also results in neuropathic pain that can be treated using the method of the invention. Nerve compression can be abrupt, as in the case of traumatic nerve crush, or can be prolonged and moderate, secondary to tumor growth or scar formation in the proximity of a major nerve bundle. Compression neuropathy can occur as a result of changes in blood flow to a nerve, causing severe ischemia and consequent nerve injury (Myers, supra (1995)).

IV. Methods of Treatment

Embodiments of the present disclosure relate to treatment of a subject. As used herein, the term subject is not intended to be limited to humans, but may also include animals, plants, or any biological organism with a neuronal or neuronal-like cells. In some embodiments, the subject is a mammalian subject in need of relief of neuropathic pain.

In some embodiments, the present disclosure provides for a method to relieve neuropathic pain, comprising optically silencing pain-associated neurotransmission in a mammalian subject in need of such relief.

In some embodiments, the present disclosure provides for a method to relieve neuropathic pain, comprising optically silencing the activities of neurons that generates pain in a mammalian subject in need of such relief.

A. Gene Therapy Targeting the DRG

Figure 7:
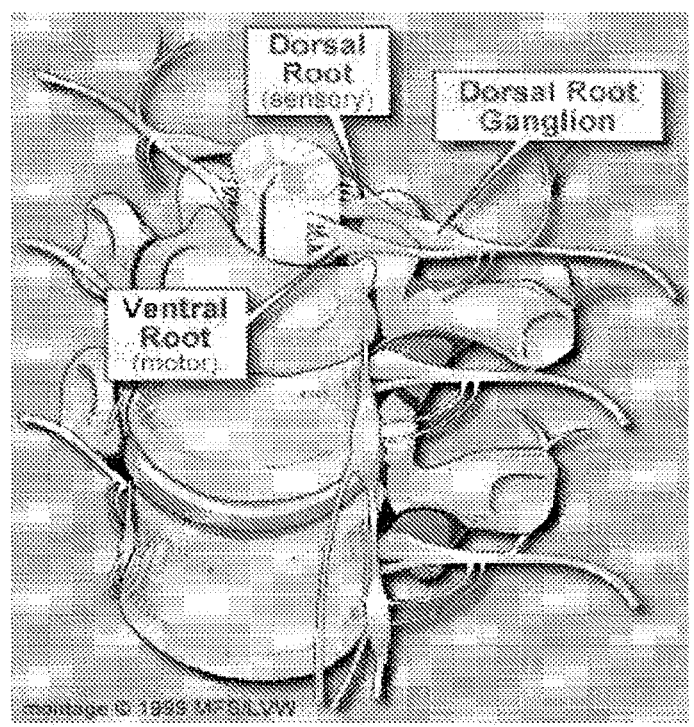
FIG. 7 depicts an exemplary embodiment of the invention where selective silencing of the dorsal (sensory) root and avoidance of the ventral (motor) root is accomplished through the use of cell specific promoters to target opsin transgene to the appropriate cell type.
Figure 8A:
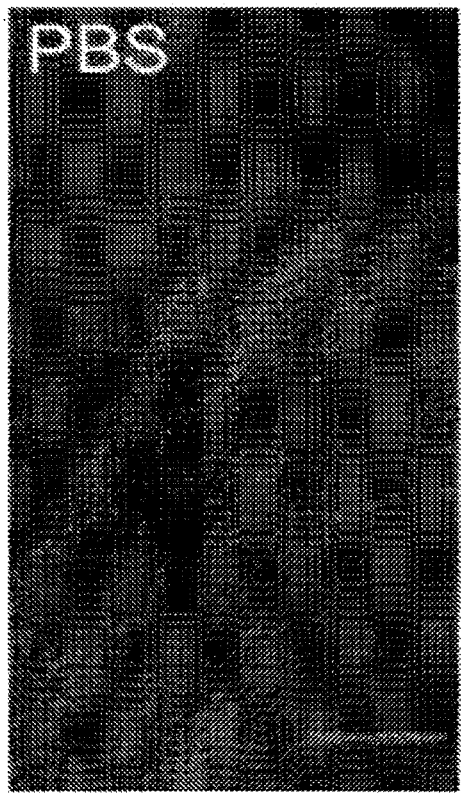
FIGS. 8A-8D depict fluorescent images showing strong, specific transduction demonstrated exclusively in DRG neurons via fluorescence vs. control. The marker gene EGFP is delivered by sc-rAAV8 vector under control of the CMV promoter/enhancer.
Figure 8B:
Figure 8C:
Figure 8D:
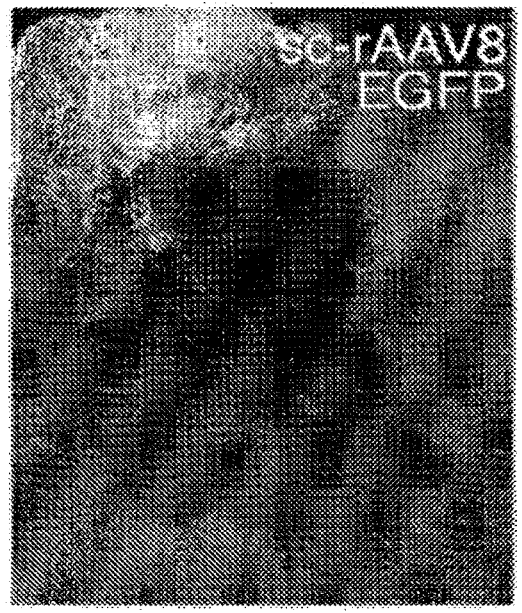

In the spinal cord, the dorsal (rear) root is the sensory root that mediates pain neuro-transmission (FIG. 7). The ventral (front) root is the motor root used for movement. This therapy will avoid silencing of the ventral (motor) root through the use of regulatory regions (promoters) selective for WDR or DRG neurons. The dorsal root ganglion contains cell bodies of general somatic afferent (inbound) neurons, mediates pain and temperature and synapse in the dorsal horn of the spinal cord. A-delta fibers are myelinated (insulated with a myelin sheath). The pain is fast and well localized, like the initial prick or stinging sensation following an injury. C fibers are nonmyelinated and smaller than A-delta fibers. They transmit pain much slower. The pain is more lasting, generalized and described as a dull ache (Table 1).

TABLE 1

Distinction between the roles of the Dorsal and Ventral Roots of the spinal cord.

|  | Dorsal Root | Ventral Root |
| --- | --- | --- |
| Synonym | Back | Front |
| Role | Sensation | Movement |
| Nerve Diameter | 0.25-1.5 µm | 1.00-5.0 µm |
| Signal Rate | 0.25-1.5 m/s | 6-10 m/s |
| Diameter | 0.25-15 µm | 1.00-5.0 µm |
| Sensation Speed | Slow pain | Fast pain |
| Duration | Lasting | Stinging |
| Sensation Region | Generalized | Localized |
| Sensation Type | Dull Ache | Prick |
| Fiber Type | Non-myelinated | Myelinated |

Acute and chronic pain are driven primarily by activation of peripheral afferent nociceptive neurons. These nerve fibers pass through the dorsal root ganglion carrying information to the spinal cord, which may transmit noxious input or hypersensitivity to normal input. The chronic sensation of pain in the absence of noxious input can result from uninhibited spontaneous firing of nociceptive neurons in the DRG or in presynaptic regions. The present invention provides methods to restore inhibition to these neurons, thereby returning their resting membrane polarization state to physiologically normal potential levels. Previous studies have demonstrated that optical control of neural activity in the CNS using light is feasible and efficacious. WO/2010/011404. It has been disclosed an excitatory cation channel (channelrhodopsin-2, ChR2) specifically to depolarizing bipolar neurons in multiple mouse models of retinal degeneration using a highly specific and efficient AAV vector containing the metabotropic glutamate receptor type 6 (GRA/16) regulatory region. This treatment effectively restored the ability for genetically blind mice to perform a visually guided behavioral task. In other studies, we have virally expressed both excitatory cation channels (ChR2) and inhibitory chloride pumps (halorhodopsin, NpHR) in multiple brain regions to control neuronal firing. Furthermore, the present invention provides compact high output implantable fiber optic light sources to optically modulate neural activity in vivo. The present invention provides the combination of the above described gene delivery, optical neuromodulation, and fiber optic hardware technologies to address a currently unmet medical need. Efficient DRG transduction has been previously demonstrated using AAV8 vectors. Additionally, the preprotachykinin-A (PPT) promoter has been demonstrated to drive neuronal specific expression in substance-P expressing neurons of the DRG when intrathecally delivered via AAV. In some embodiments, intrathecal injection of an AAV8-CAG-GFP vector is used, which provides efficient transduction of in vivo sensory neurons.

In another aspect, the present invention provides gene therapy targeting the DRG. Separation of wanted and unwanted opioid effects can be achieved on anatomic grounds: Untoward effects, such as sedation, are mediated by the forebrain, whereas the desired analgesic effect can be achieved by selectively enhancing opioid activity at the spinal "pain gate".

Intrathecal (IT, i.e., spinal cord) opioid administration is one such strategy. It is highly effective because µ-opioid receptors localized at the spinal level induce profound analgesia without marked effects. As analgesia after a single IT opioid administration lasts only a few hours, prolonged pain control requires the implantation of a pump and a permanent IT catheter. Although this approach has been shown to provide superior pain control in a randomized controlled clinical trial, Smith, T. J., el al. *J Clin Oncol* 20, 4040-4049 (2002), the method has not been adopted outside of few specialized medical centers fielding multi-specialty teams consisting of anesthesiologists, neurosurgeons and oncologists, who are able to service the implanted hardware and investigate acute complications, which might be related to the catheter.

Figure 3:
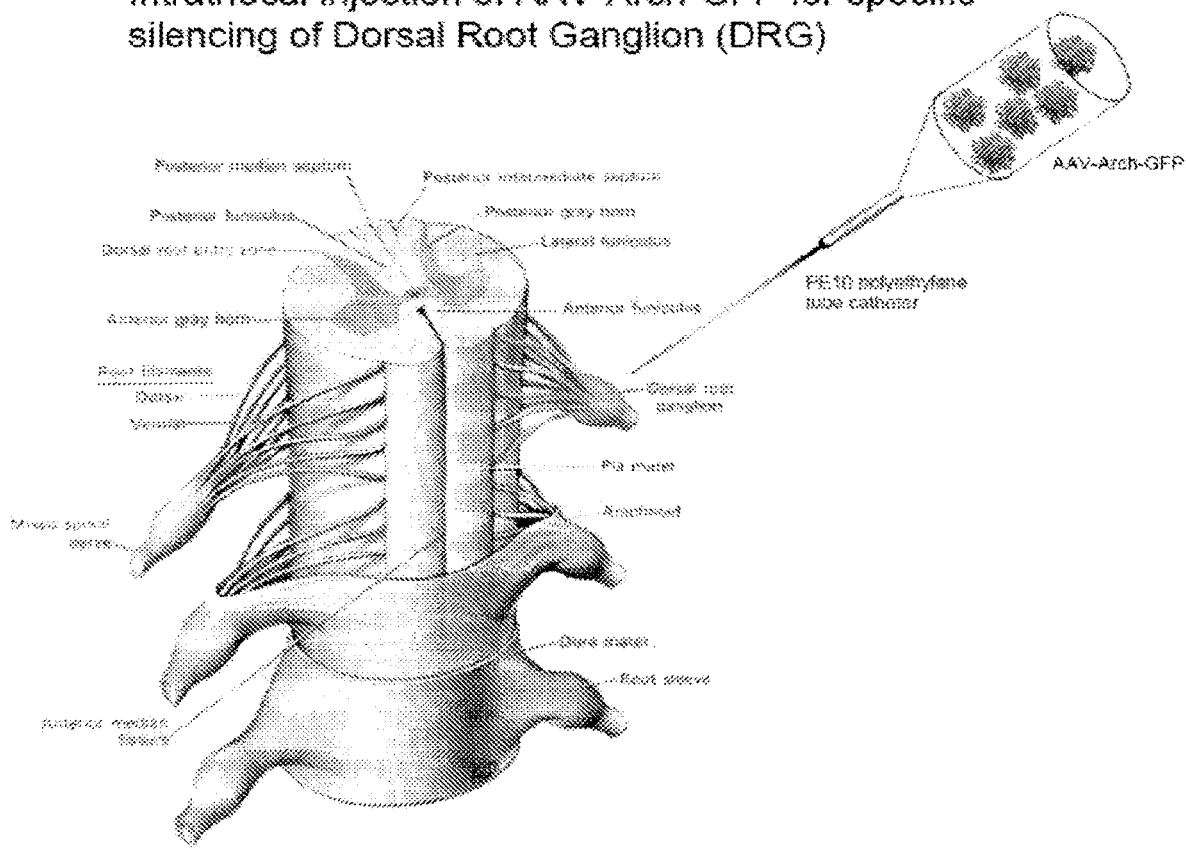
FIG. 3 depicts the transduction of DRG following intrathecal injection (lumbar puncture) of AAV-Arch-GFP using a polyethylene tube catheter.

In some embodiments, the present invention provides compositions and methods for a single-dose, IT administration of an AAV containing an optical silencer mediates pain relief over a long time period, which reduces side effects and improve quality of life by freeing patients from external pumps and hazardous procedures (FIG. 3). Certain gene products may not have a conventional drug equivalent, for example, certain larger proteins may not be available as a recombinant product or a small-molecule analog, but can be encoded and delivered as a therapeutic gene in a vector as provided herein.

In some embodiments, the method comprises expressing in a cell of a subject a recombinant nucleic acid and controlling the neural activity of said cell with a light beam to modulate the expression of a light-sensitive protein, thereby relieving neuropathic pain in the subject. The method provides significant analgesia for chronic neuropathic pain without off-target effects, such as general central nervous system depression. In some embodiments, the method provides 1,5,10, 15, 20, 30, 40, 50, 60, 70, 80, 90 percent reduction in the neuropathic pain.

In some embodiments, a neuron derived from the subject in need of treatment, or a host other than the subject, is transduced with a nucleic acid encoding a light-sensitive protein provided herein, preferably in a viral vector, and the transduced neuron is transplanted to the subject in need of treatment.

The ability of a given method to modulate pain can be quantified by using any one of the following tests: tight ligation of L6 and L7, as a model of neuropathic pain; complete Freund's adjuvant into knee joint or hind paw as a model of Long term inflammatory pain (Palecek, J. (1992) Neurophysiol 68:1951-66); nerve ligation (CCI); thermal hyperalgesia, tactile allodynia and cold allodynia (Carlton, S. M. et al. (1994) Pain 56:155-66); thermal paw withdrawal latency (Hargreaves test); von Frey mechanical withdrawal threshold; the hot-plate latency test; the tail flick test (Stone, L. S., et al. (1997) NeruroReport 8:3131-3135); the warm-water immersion tail flick assay (Stone, L. S., et al. (1997) NeruroReport 8:3131-3135); the crush injury to the sciatic nerve test (De Konig, et al. (1986) J. Neurol. Sci. 74:237-246); the cold water allodynia test (Hunter, et al. (1997) Pain 69:317-322; the paw pressure latency assay (Hakki-Onen, S., et al. (2001) Brain Research 900(2):261-7; or the radiant heat test (Yoshimura, M., (2001) Pharm. Research 44(2): 105-11).

The measure of pain responses will be conducted through behavioral assays that measure motor responses (i.e., limb retraction to a noxious stimulus). Le Bars et al., Pharmacological Reviews, 2001 53(4)597-652. In future studies in human subjects, measures of pain response will be conducted through subjective rating scales.

B. Vector Delivery by the Intrathecal Route (Lumbar Puncture)

In another aspect, the present invention provides compositions and methods for the delivery of the vector by the Intrathecal Route (lumbar puncture).

Figure 2:
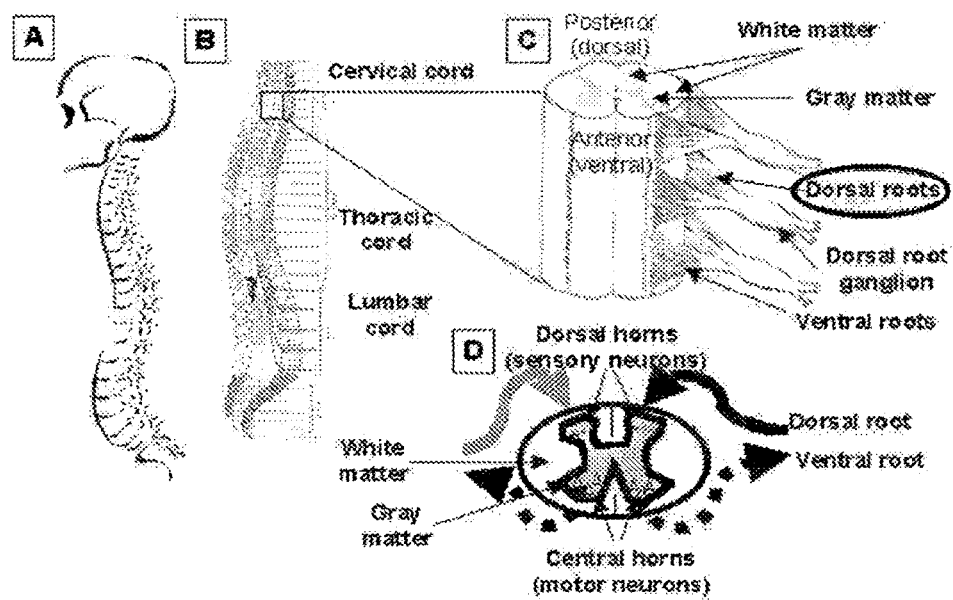
FIG. 2 depicts the location of the Dorsal Root Ganglion (DRG) in the spinal cord. The dorsal root in the dorsal horn contains sensory neurons, while the ventral root in the central horn contains motor neurons.

Nervous system gene therapy (that is, in vivo gene transfer) has possible benefits, such as to improve upon traditional forms of drug delivery, for example, reaching the brain-side of the blood-brain barrier (BBB); providing a prolonged (or indefinite) drug/gene effect; targeting drug/gene activity to a desired anatomical site; reducing side effects; and freeing patients from repeat injections, external pumps and hazardous procedures. These goals may be most attainable by gene delivery through a clinically established procedure that is widely available. Suitable techniques include, but are not limited to, lumbar puncture (LP). LP is the technique to access the sensory afferents of the spinal cord and DRG safely at the bedside (FIG. 2).

C. Optical Control

Technological advances in neuroscience have enabled the ability to optically control neural activity precisely with visible light. Central to this technology is the expression of microbial opsin genes that encode photosensitive ion channels and pumps. Boyden, E. S. et al., Nat Neurosci 8, 1263-1268 (2005); Han, X. & Boyden, E. S. PLoS ONE 2, e299 (2007); Han, X., et al., Neuron 62, 191-198 (2009); Lagali, P. S., et al., Nat. Neurosci. (2008). When expressed in mammalian neurons, these optical neuromodulators enable the complete control of neural activity with extremely high spatial and temporal precision. Furthermore, these opsins can be genetically targeted and stably expressed in desired cell populations using non-pathogenic adeno-associated viral (AAV) vectors containing select genetic regulatory sequences. Lagali, P. S., et al., Nat Neurosci (2008); Flannery, J. G. & Greenberg, Neuron 50, 1-3 (2006); Greenberg, K. P., et al., Association of Research in Vision and Ophthalmology (2007); Horsager, A., et al. Association of Research in Vision and Ophthalmology (2009).

A method of optically controlling neural activity in a cell, comprising expressing in the cell a recombinant nucleic acid comprising the coding region for a light-sensitive protein, and controlling the neural activity of the cell with a light beam to modulate the expression of the light-sensitive protein.

High spatial and temporal precision can be controlled through the employment of precise activation of the LED array. This would include the stimulation pulse duration (i.e., duration the LED stimulus would be activated), inter-pulse duration (i.e., frequency or pulse train rate), space constant of activation (i.e., how far apart the LED stimuli should be to be effective), and amplitude of light stimulus.

In some embodiments, the extent of silencing is dynamically controlled via a variable intensity optical source. In some embodiments, the optical source comprises an implantable 1- or 2- or 3-dimensional fiber optic device. The stimulation patterns presented by the device can be controlled in both the time and space dimensions. For example, stimulation patterns from a specific location on the optical fiber of LED can be modulated in terms of pulse duration and frequency. In the space dimension, the activation of different LEDs can be controlled both in terms of location (i.e., which LEDs or optical fiber locations are active at each point in time) and amplitude (i.e., intensity).

In some embodiments, the controlling is carried out with high spatial and temporal precision using a specifically positioned device where the light emission is controlled over time. Some embodiments employ a 1 or 2-dimensional array of light stimulation, with the temporal pattern of activation controlled through modulation of the pulse train from each LED. See, e.g., US Application Publications Nos. US20080125832A1 and US20090312818A1 for more details.

V. Pharmaceutical Compositions

Embodiments of the present disclosure provide for a pharmaceutical composition, comprising a recombinant nucleic acid and a pharmaceutically acceptable carrier.

Compositions according to the present disclosure are effective for treating neuropathic pain. Examples of the neuropathic pain include neuropathic pains in postherpetic neuralgia, trigeminal neuralgia, diabetic neuralgia, cancer pain, persistent postoperative or posttraumatic pain, hyperalgia, allodynia, postthoracotomy pain, CRPS, pain associated with multiple sclerosis, AIDS, thalamic pain, paraplegic pain caused by myelopathy, anesthesia dolorosa, phantom limb pain, and the like.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, rectal administration, and direct injection into the affected area, such as direct injection into a tumor. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for internal use include sterile aqueous solutions or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the internal compositions can be brought about by including in the composition an agent which delays absorption, for example, aluminum monostearate and gelatin.

Sterile solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Methods of administering agents according to the present invention are not limited to the conventional means such as injection or oral infusion, but include more advanced and complex forms of energy transfer. For example, genetically engineered cells that carry and express energy modulation agents may be used. Cells from the host may be transfected with genetically engineered vectors that express bioluminescent agents. Transfection may be accomplished via in situ gene therapy techniques such as injection of viral vectors or gene guns, or may be performed ex vivo by removing a sample of the host's cells and then returning to the host upon successful transfection. Such transfected cells may be inserted or otherwise targeted at the site where diseased cells are located. In this embodiment, the initiation energy source may be a biochemical source as such ATP, in which case the initiation energy source is considered to be directly implanted in the transfected cell. Alternatively, a conventional micro-emitter device capable of acting as an initiation energy source may be transplanted at the site of the diseased cells.

VI. Kits

Compositions and reagents useful for the present invention may be packaged in kits to facilitate application of the present invention. In some embodiments, the present method provides for a kit comprising a recombinant nucleic acid of the invention. In some embodiments, the present method provides for a kit comprising a recombinant virus of the invention. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose, to calculate and control intensity of a light source.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1 rAAV Modifications to Increase IT Gene Transfer Efficacy

Conventional single-stranded rAAV2 vectors perform poorly after IT delivery in rats; expression can be detected only by highly sensitive methods like quantitative PCR even after administration of high vector doses. Confronted with this finding, we reasoned that rAAV2 could fail because of two roadblocks: Firstly, failure of target cells to take the vector up due to lack of compatible cell surface receptors, and secondly, second-strand DNA synthesis, which could be a limiting step especially in a quiescent tissue. Pseudotyping of rAAV with capsids of serotypes 1, 3 and 5 was tested alone or in combination with a modification of the ITR. The former alters vector tropism and the latter allows packaging of sc-rAAV vectors. Combining both types of modification led to the identification of sc-rAAV1 as a vector that performed superiorly in the IT space. IT delivery of $3 \times 10^9$ sc-rAAV1 particles per animal led to stable expression of enhanced green fluorescent protein (EGFP) for 3 months detectable by Western blotting, quantitative PCR, and in a blinded study by confocal microscopy. Expression was strongest in the cauda equina and the lower sections of the spinal cord, and only minimal in the forebrain. Storek, B., et al., *Mol Pain* 2, 4 (2006). Serotype 5 performed favorably in the same study but seemed to be substantially weaker than serotype 1. In a subsequent study, which will be discussed in detail below, we found that serotype 8 performed even better than any of the previously tested capsids and thereby became the basis of our current vectors.

Similar findings regarding the choice of serotype and the use of sc-vectors were reported after intraocular injection of AAV. AAV8 vectors yielded greater transduction efficiency than AAV2 and AAV5, and the self-complementary variants of AAV8 and AAV2 exhibited earlier onset and higher transgene production than the respective single-stranded vector. Natkunarajah, M., et al., *Gene therapy* 15, 463-467 (2008).

Example 2

Targeting of DRG Neurons

One property of rAAV vector modified as above, that is, sc-rAAV1 and sc-rAAV8, was their remarkable ability to express the recombinant transgene highly effectively, and almost exclusively (>99%) in the primary sensory neurons. This was unexpected, because IT administration of other vectors fails to target neurons (for example, plasmids or adenovirus transduce meningeal fibroblasts). Primary sensory neurons are, perhaps, the ideal target for pain gene therapy. This point has been shown by a long series of studies with herpes simplex virus, a vector that targets sensory neurons if administered subcutaneously. Microscopic examination of the brain, spinal cord, DRGs, nerve roots and meningeal linings 1 month after administration of sc-rAAV8 expressing the marker gene EGFP (under the control of the CMV promoter/enhancer) revealed strong specific EGFP fluorescence, exclusively in DRG neurons and their axons, and dendrites entering and exiting the DRG (FIG. 8). Examination of the spinal cord showed EGFP fluorescence diagrammatically outlining the course of primary sensory neuron axons, which enter the spinal cord through the posterior nerve root, project into the posterior horn and form the fasciculus gracilis of the posterior column. Among DRG neurons, all immunohistochemical distinct subpopulations tested were found to be transduced, namely cells positively stained for nociceptive-neuron marker vanilloid receptor suptype 1 (TRPV1), for the small peptidergic-neuron markers substance P and calcitonin gene-related peptide and the non-peptidergic-neuron marker griffonia simplicifolia isolectin B4.

Example 3

Testing in a Rat Neuropathy Model

Beutler, A. S., et al., J Neurochem 64, 475-481 (1995) chose the L5 spinal nerve ligation (SNL) rat model of neuropathic pain, Chung, J. M., et al., Methods Mol Med 99, 35-45 (2004), to assess the efficacy of IT sc-rAAV8 for pain using two different known analgesic genes, namely preprobeta-endorphin (ppβEP) and recombinant interleukin-10 (rIL-10). ppβEP is an artificial gene that has been developed earlier y this group. It was found to induce secretion of PEP, which acts as μ-opioid receptor agonist. Beutler, A. S., et al., J Neurochem 64, 475-481 (1995); Finegold, A. A., et al., Human gene therapy 10, 1251-1257 (1999). Additionally, one could consider the use of a transgene whose anti-allodynic activity may not rely on opioid receptor activation. As an example, Beutler et al. chose rIL-10, which is believed to exert its known analgesic activity in neuropathic pain through suppression of glial activation through its anti-inflammatory activity. Beutler, A. S., et al., Current opinion in molecular therapeutics 7, 431-439 (2005). IT administration of sc-rAAV8/ppβEP and of sc-rAAV8/rIL10 both led to a significant attenuation of allodynia in the SNL model. Therapeutic activity set in at 1-month post IT delivery and persisted until the predefined end point of the study at 3-month post IT delivery. In a subsequent experiment determining the expression kinetics of IT sc-rAAV8, the onset of expression occurred between 0.5 and 1 month. Hence, the delay in the onset of anti-allodynic activity was due to the gradual onset of transgene expression, that is, the type of delayed onset of activity that is universally observed with AAV vectors, as discussed in an earlier section.

Beutler, A. S., et al., Current opinion in molecular therapeutics 7, 431-439 (2005).

Example 4

Nocicpetor Cell Examination and Culture

Pain cells (nociceptors) are difficult to examine, but this has been done previously (FIG. 9). Their most interesting parts—the sensory endings—are very thin fibers, embedded in a tough layer of skin tissue. Conventional methods for physiological experimentation like calcium imaging or electrophysiology can hardly be applied to these fibers. Consequently, there is little direct physiological information about what happens when painful stimuli hit the skin. One approach to this problem is to isolate the somata of pain cells out of the dorsal root ganglia, to keep them in primary culture, and to study transduction proteins in these cultured neurons. The basic assumption is that the cultured pain cells express the same proteins that mediate pain transduction the sensory endings in vivo.

The dorsal root ganglia (DRG) contain the cell bodies of nociceptors. A bifurcated axon emanates from each cell body. At its central end this axon forms a synapse within the spinal cord, the peripheral, sensory ending lies in the skin or in other pain-sensitive tissues. Primary cultures from dorsal root ganglia grow well on a surface covered with laminin, an extracelluar matrix protein. Non-neuronal cells grow a dense carpet over the entire surface and form a support on which pain cells (large, round cells) can live for several weeks. Pain cells often grow neurites which connect several cells, a process which is promoted by neuronal growth factors.

Example 5

Figure 12:
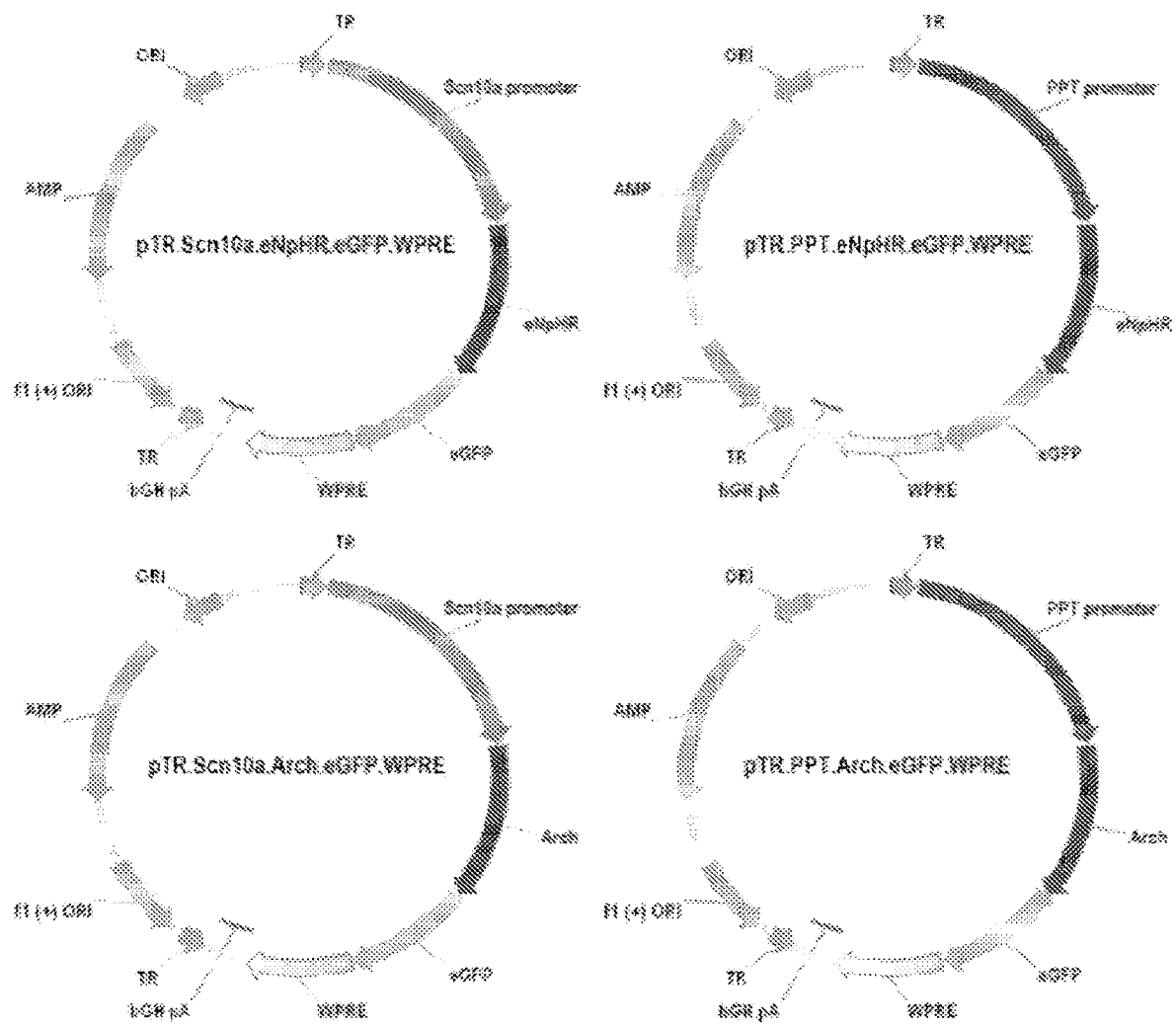
FIG. 12 depicts self complimentary AAV transfer vectors containing the DRG specific regulatory promoter regions from Scn10a or PPT driving expression of either enhanced halorhodopsin (eNpHR) or archaerhodopsin (Arch) fused to eGFP. These transfer vectors is packaged into AAV (i.e. AAV8) capsids for efficient transduction of pain pathway neurons in vivo according to some embodiments of the invention.

The following sequences and maps represent examples of nucleic acids that enable the selective expression of silencing opsins in nociceptive neurons of the DRG. The preprotachykinin-A (PPT) promoter has been demonstrated to drive neuronal specific expression when delivered via AAV (FIG. 10). Harrison, P. T., et al., *Neuroscience* 94, 997-1003 (1999). Furthermore, the voltage-gated sodium channel subunit alpha (Scn10a) has also been shown to be selectively expressed in DRG neurons (FIG. 11). Puhl, H. L., 3rd & Ikeda, S. R., *J Neurochem* 106, 1209-1224 (2008). These promoters are incorporated into self complimentary AAV vectors containing silencing opsin transgenes such as halorhodopsin (eNpHR), archaerhodopsin-3 (Arch), and *Leptosphaeria maculans* (Mac) (FIG. 12).

Example 6

Figure 13A:
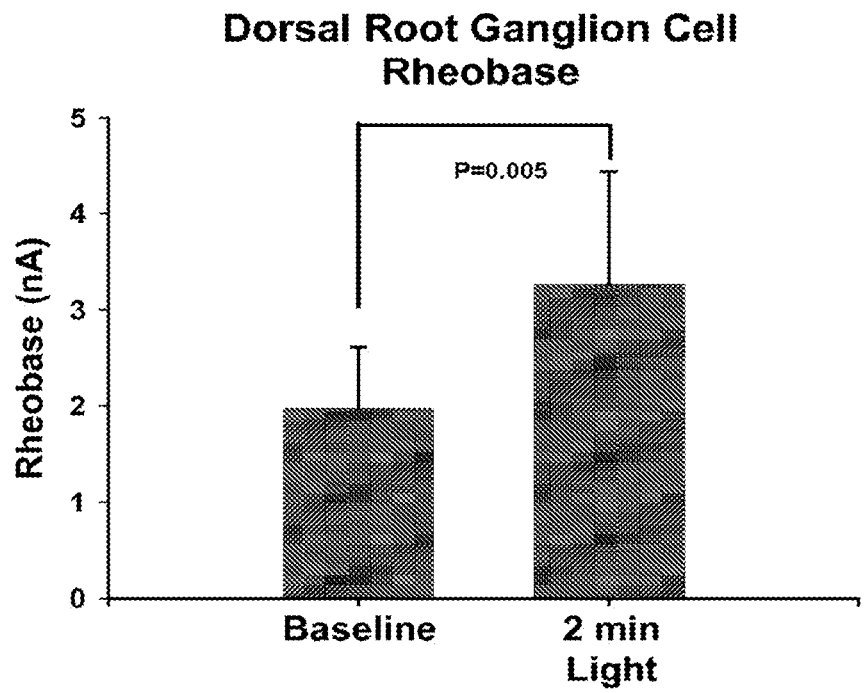
FIGS. 13A and 13B depict reduction in A) minimum spiking level (rheobase) and B) resting membrane potential for dorsal root ganglion (DRG) cells transduced with AAV8 carrying the CAGG-ArchT-GFP vector, following exposure to green light.
Figure 13B:
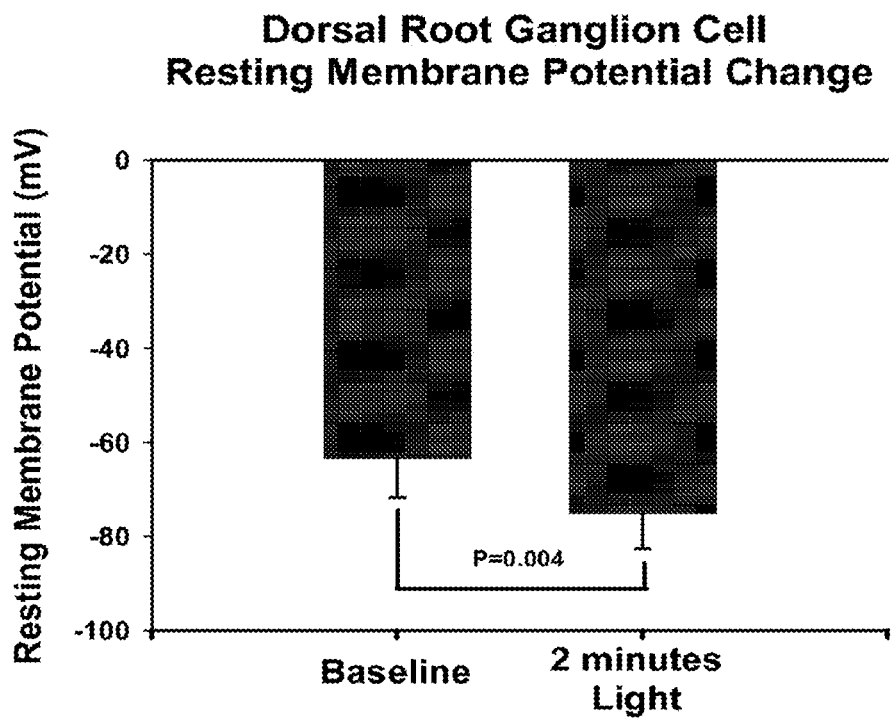

Reduction in hyperexcitability of dorsal root ganglion cells (DRG) was achieved using light-activated methods of the invention, with results shown in FIGS. 13A-B. 11 different DRG cells were transfected in vivo with an AAV8 vector carrying the CAGG-ArchT-GFP vector. Following isolation, recordings to measure rheobase (FIG. 13A) and resting membrane potential (FIG. 13B) were conducted ex vivo, with or without exposure to green light. Rheobase refers to the minimum spiking level upon injection of current.

Current was injected into the cells recorded for FIG. 13A to create spiking activity. The y-axis is nanoamps of current. In the baseline condition (untreated tissue, no ArchT), rheobase was approximately 2 nanoamps. When tissue was transduced with AAV8 (CAGG-ArchT-GFP) and was exposed to green light, the rheobase was increased to approximately 3.5 nanoamps. This shows that ArchT expressing DRG require more current for activation than DRG not expressing ArchT, establishing that ArchT, coupled with green light exposure, can silence activity in these cells.

FIG. 13B shows measurements taken from the same 11 cells as shown in FIG. 13A. Here, ArchT expression coupled with green light exposure leads to a decrease in resting membrane potential. This shows that ArchT+green light causes a increase in intracellular negativity, another measure that shows this method can decrease the activity of these treated cells.

What is claimed is:

1. A method to relieve neuropathic pain in a subject in need of such relief, comprising
transfecting dorsal root ganglion (DRG) neurons of the subject with a polynucleotide using an adeno-associated viral (AAV) vector by intrathecal injection, wherein the polynucleotide comprises a regulatory region driving expression of a sequence encoding archaerhodopsin-3 (Arch) and the regulatory region comprises at least one of a preprotachykinin-A (PPT) promoter, a voltage-gated sodium channel subunit alpha (Scn10a) promoter, and a vanilloid receptor subtype 1 (TRPV1) promoter, and exposing Arch-expressing DRG neurons to light comprising a wavelength of from 495-570 nm, wherein the exposing Arch-expressing DRG neurons to light leads to a decrease in membrane potential relative to DRG neurons not expressing Arch.

2. The method of claim 1, wherein the method does not provide off-target effects.

3. The method of claim 1, wherein the method does not provide general central nervous system depression.

4. The method of claim 1, wherein exposing comprises directly illuminating a DRG.

5. The method of claim 1, wherein the regulatory region comprises a preprotachykinin-A (PPT) promoter.

6. The method of claim 1, wherein the AAV vector is a self-complementary recombinant adeno-associated virus serotype 1 (sc-rAAV1) or a self-complementary recombinant adeno-associated virus serotype 8 (sc-rAAV8).

7. The method of claim 1, wherein the AAV vector is an AAV8 vector.

8. The method of claim 1, wherein the AAV vector is an AAV1 vector.

9. The method of claim 1, wherein AAV vector is a self-complementary recombinant adeno-associated virus serotype 1 (sc-rAAV1).

10. The method of claim 1, wherein AAV vector is a self-complementary recombinant adeno-associated virus serotype 8 (sc-rAAV8).

11. The method of claim 1, wherein the regulatory region comprises a voltage-gated sodium channel subunit alpha (Scn10a) promoter.

12. The method of claim 7, wherein the regulatory region comprises a preprotachykinin-A (PPT) promoter.

13. The method of claim 8, wherein the regulatory region comprises a preprotachykinin-A (PPT) promoter.

14. The method of claim 9, wherein the regulatory region comprises a preprotachykinin-A (PPT) promoter.

15. The method of claim 10, wherein the regulatory region comprises a preprotachykinin-A (PPT) promoter.

16. The method of claim 7, wherein the regulatory region comprises a voltage-gated sodium channel subunit alpha (Scn10a) promoter.

17. The method of claim 8, wherein the regulatory region comprises a voltage-gated sodium channel subunit alpha (Scn10a) promoter.

18. The method of claim 9, wherein the regulatory region comprises a voltage-gated sodium channel subunit alpha (Scn10a) promoter.

19. The method of claim 10, wherein the regulatory region comprises a voltage-gated sodium channel subunit alpha (Scn10a) promoter.

* * * * *